United States Patent [19]

Hamanaka et al.

[11] 4,346,087
[45] Aug. 24, 1982

[54] ANTIBACTERIAL SURFACE ACTIVE AGENT CONTAINING AZAALKENELACTAM

[75] Inventors: Hiroyoshi Hamanaka, Yachio; Mamoru Shinano, Negishi, both of Japan

[73] Assignee: Toho Chemical Industry Co., Ltd., Japan

[21] Appl. No.: 224,520

[22] PCT Filed: Mar. 28, 1980

[86] PCT No.: PCT/JP80/00055
§ 371 Date: Dec. 1, 1980
§ 102(e) Date: Dec. 1, 1980

[87] PCT Pub. No.: WO80/02155
PCT Pub. Date: Oct. 16, 1980

[30] Foreign Application Priority Data

Mar. 30, 1979 [JP] Japan .................................. 54/38254

[51] Int. Cl.³ ..................... A61K 31/55; C07D 243/08
[52] U.S. Cl. ............................... 424/244; 260/239.3 R
[58] Field of Search ................. 260/239.3 R; 424/244

[56] References Cited

U.S. PATENT DOCUMENTS 3,419,548 12/1968 Gatzi et al. .................. 260/239.3 R

FOREIGN PATENT DOCUMENTS 39-29848 12/1964 Japan .................................. 546/243
43-26176 11/1968 Japan ......................... 260/239.3 R Primary Examiner—Robert T. Bond Attorney, Agent, or Firm—Karl W. Flocks; Sheridan Neimark

[57] ABSTRACT

An antibacterial surface active agent comprising an effective amount of at least one cyclic amide represented by the general formula

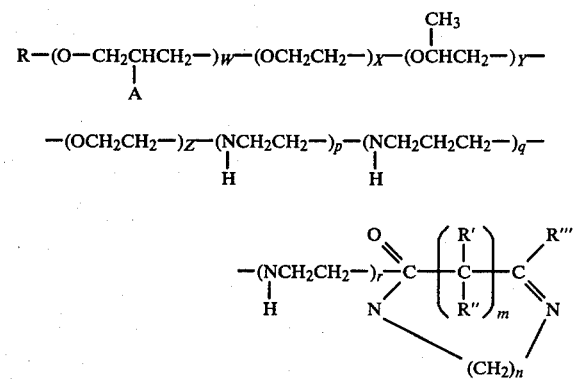

wherein R is an alkyl group, alkenyl group, alkylaryl group, alkylarylalkyl group, hydroxyalkyl group, acyl group or hydroxyl-substituted acyl group having 8 to 22 carbon atoms in total, R', R" and R''' are hydrogen atoms or methyl groups, A is hydrogen atom or methyl group, $0 \leq W \leq 1$, $0 \leq X+Z \leq 3$, $0 \leq Y \leq 3$, $0 \leq p+q+r \leq 3$, $m=1$ or $2$ and $n=2$ or $3$; said compound may assume a structure in which, if necessary, the nitrogen atoms, except for the amide grouping, may combine with an organic acid radical by covalent bond or to add to an organic or inorganic acid.

21 Claims, 5 Drawing Figures

ANTIBACTERIAL SURFACE ACTIVE AGENT CONTAINING AZAALKENELACTAM

TECHNICAL FIELD

This invention relates to novel antibacterial surface active agents containing novel cyclic amides. More particularly, the antibacterial surface active agent of this invention comprises a compound which has in the same molecule a hydrophobic group comprising a chain of 8 to 22 carbon bonds and a hydrophilic group as shown below, comprising a 7= or 8=1=membered lactam group containing a basic nitrogen atom,

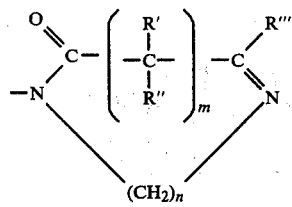

wherein R', R" and R'" are hydrogen atoms or methyl groups, m=1 or 2 and n=2 or 3; said compound may assume a structure which allows the compound to combine at the position of said basic nitrogen atom with an organic acid radical by covalent bond or to add to an organic or inorganic acid.

DISCLOSURE OF THE INVENTION

As a result of extensive studies, the present inventors confirmed by IR, NMR and mass spectral analyses of the reaction products that on reacting an acetoacetic ester or formylpropionic ester of a lower alcohol with a polyamine having primary amino groups and secondary amino groups which are interposed therebetween with 2 or 3 methylene radicals there is formed at first a nitrile bond by the reaction between said primary amino group of the polyamine and the carbonyl group of the ketone or aldehyde, followed by the formation of a lactam group by the reaction between said secondary amino group and the carbonyl group of the ester in the same molecule; they further confirmed by neutralization titration using an organic and an inorganic acids that the nitrogen forming said nitrile bond has a basic property, and found that the reaction products including those having an organic acid radical obtained by the reaction of a monohalocarboxylic acid with said nitrogen have a surface activity at the liquid-water interfaces and have an antibacterial activity, too.

More particularly, the antibacterial surface active compound of this invention is a cyclic amide represented by the general formula

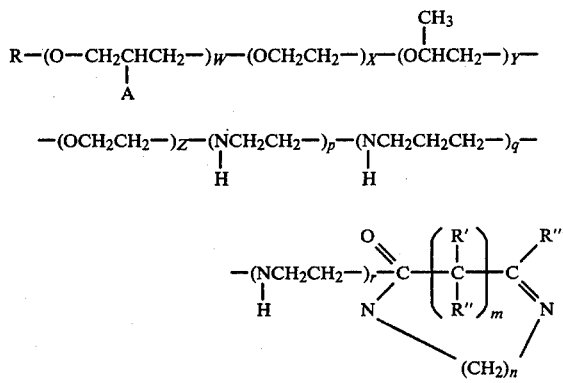

(wherein, R is an alkyl group, alkenyl group, alkylaryl preferably monoalkylphenyl group, alkylarylalkyl preferably monoalkylbenzyl group, hydroxyalkyl group, acyl preferably alkylcarbonyl or alkenylcarbonyl group, or hydroxyl-substituted acyl preferably hydroxyl-substituted alkycarbonyl or alkenylcarbonyl group having 8 to 22 total carbon atoms, R', R" and R'" are hydrogen atoms or methyl groups, A is hydrogen atom or hydroxyl group, $0 \leq W \leq 1$, $0 \leq X+Z \leq 3$, $0 \leq Y \leq 3$, $0 \leq p+q+r \leq 3$, m=1 or 2, and n=2 or 3; said cyclic amide may have a structure which, if necessary, allows the nitrogen atoms, except for the amide group, to combine with an organic acid radical by covalent bond or to add to an organic or inorganic acid) which is formed by reacting an acetoacetic ester or formylpropionic ester of an alcohol having 4 or less carbon atoms with at least one compound represented by the general formula

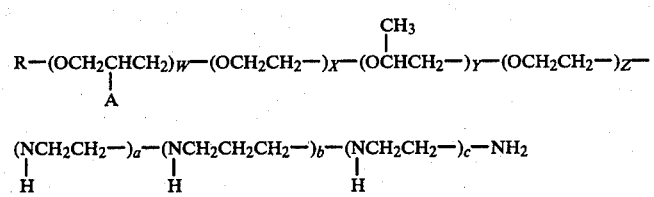

(wherein R is an alkyl group, alkenyl group, alkylaryl preferably monoalkylphenyl group, alkylarylalkyl preferably monoalkylbenzyl group, hydroxyalkyl group, acyl preferably alkyl- or alkenylcarbonyl group, or hydroxyl-substituted acyl preferably hydroxy-substituted alkyl- or alkenylcarbonyl group having 8 to 22 total carbon atoms, A is hydrogen atom or hydroxyl group, $0 \leq W \leq 1$, $0 \leq X+Z \leq 3$, $0 \leq V \leq 3$, $1 \leq a+b+c \leq 4$) composed of a terminally monoalkylated polyalkylenepolyamine (the hydrocarbon radicals include alkyl groups, alkenyl groups, alkylaryl preferably monoalkylbenzyl groups, alkylarylalkyl preferably monoalkylbenzyl groups, hydroxyalkyl groups, alkoxyalkyl groups, alkoxyhydroxyalkyl groups, etc.), said polyalkylenepolyamine being obtained by the addition of 1 to 3 moles of ethyleneimine to 1 mole of ethylenediamine or 1,3-propylenediamine or by the addition of acrylonitrile to said diamine followed by hydrogenation, said addition and hydrogenation being repeated 1 to 3 times (in each reaction cycle, 1 mole of acrylonitrile and 2 moles of hydrogen are used for 1 mole of the amine used as starting material) or by carrying out the above both reactions; a polyalkylenepolyamine (the hydrocarbon groups thereof include alkyl groups, alkenyl groups, hydroxyalkyl groups, hydroxyalkenyl groups, etc.); and a monoalkylated (the hydrocarbon groups thereof include alkyl groups, alkenyl groups, alkylaryl preferably monoalkylphenyl groups, alkylarylalkyl preferably monoalkylbenzyl groups, hydroxyalkyl groups, alkoxyalkyl groups, alkoxyhydroxyalkyl groups, etc.) ethylenediamine and 1,3-propylenediamine; or formed by reacting an acetoacetic ester or formylpropionic ester of an alcohol having 4 or less carbon atoms with 1, 2, or more polyalkylenepolyamines obtained by the addition of 1 to 3 moles of ethyleneimine to 1 mole of ethylenediamine or 1,3-propylenediamine, or by 1 to 3 cycles of the addition of acrylonitrile followed by hydrogenation (the molar ratio in each reaction cycle is 1 mole of acrylonitrile and 2 moles of hydrogen for 1 mole of the amine used as starting material), or by carrying out the above both reactions, and then, further reacting with a carboxylic acid having an alkyl, alkenyl or hydroxyalkenyl group of 7 to 21 carbon atoms; or formed by reacting an acetoacetic ester or formylpropionic ester of an alcohol having 4 or less carbon atoms with hydroxyethylated ethylenediamine, hydroxypropylated ethylenediamine, hydroxyethylated 1,3-propylenediamine and hydroxypropylated 1,3-propylenediamine and then further reacting with a carboxylic acid having an alkyl group, alkenyl group, hydroxyalkyl group or hydroxyalkenyl group and/or reacting with a monochlorinated or monobrominated carboxylic acid or a salt thereof.

As for the polyalkylenepolyamines used as starting materials for the above-said amines, mention may be made of ethylenediamine, diethylenetriamine, triethylenetetramine, tetraethylenepentamine, adduct of 1,3-propylenediamine with 1 mole ethyleneimine, adduct of 1,3-propylene diamine with 2 moles ethyleneimine, adduct of 1,3-propylenediamine with 3 moles ethyleneimine, dipropylenetriamine, tripropylenetetramine, tetrapropylenepentamine, and polyethylenepolypropylenepolyamine having 5 or less nitrogen atoms in total. As for the monoalkylated products of these amines, there may be cited monooctylated product, monononylated product, monodecylated product, monoundecylated product, monododecylated product, monotridecylated product, monotetradecylated product, monopentadecylated product, monohexadecylated product, monooctadecylated product, mono(9-octdecenyl)ated product, monoeicosylated product, monodocosylated product, mono(2-hydroxy)dodecylated product, mono(2-hydroxy)hexadecylated product, mono(2-hydroxy)tetradecylated product, mono(2-hydroxy)docosylated product, monooctoxy(2-hydroxy)propylated product, monononylphenoxy(2-hydroxy)propylated product, monododecoxy(2-hydroxy)propylated product, monooctylpoly(1–3 moles)oxyethylated product, mononoylpoly(1–3 moles)oxyethylated product, monodecylpoly(1–3 moles)oxyethylated product, monoundecylpoly(1–3 moles)oxyethylated product, monododecylpoly(1–3 moles)oxyethylated product, monotridecylpoly(1–3 moles)oxyethylated product, monotetradecylpoly(1–3 moles)oxyethylated product, monopentadecylpoly(1–3 moles)oxyethylated product, monohexadecylpoly(1–3 moles)oxyethylated product, monooctadecylpoly(1–3 moles)oxyethylated product, mono(9-octadecenyl)poly(1–3 moles)oxyethylated product, monoeicosylpoly(1–3 moles)oxyethylated product, monodocosylpoly(1–3 moles)oxyethylated product, monobutylphenylpoly(1–3 moles)oxyethylated product, monooctylphenylpoly(1–3 moles)oxyethylated product, monononylphenylpoly(1–3 moles)oxyethylated product, monooctylpoly(1–3)oxypropylated product, mononyl(1–3 moles)oxypropylated product, monodecylpoly(1–3 moles)oxypropylated product, monododecylpoly(1–3 moles)oxypropylated product, monotridecylpoly(1–3 moles)oxypropylated product, monotetradecylpoly(1–3 moles)oxypropylated product, monopentadecylpoly(1–3 moles)oxypropylated product, monohexadecylpoly(1–3 moles)oxypropylated product, monooctadecylpoly(1–3 moles)oxypropylated product, mono(9-octadecenyl)poly(1–3 moles)oxypropylated product, monoeicosylpoly(1–3 moles)oxypropylated product, monodocosylpoly(1–3 moles)oxypropylated product, monobutylphenyl(1–3 moles)oxypropylated product, monooctylphenyl(1–3 moles)oxypropylated product, monononylphenyl(1–3 moles)oxypropylated product, monooctylpoly(2–3 moles in total)oxyethyloxypropylated product, monononylpoly(2–3 moles in total)oxyethyloxypropylated product, monodecylpoly(2–3 moles in total)oxyethyloxypropylated product, monoundecylpoly(2–3 moles in total)oxyethyloxypropylated product, monododecylpoly(2–3 moles in total)oxyethyloxypropylated product, monotridecylpoly(2–3 moles in total)oxyethyloxypropylated product, monotetradecylpoly(2–3 moles in total)oxyethyloxypropylated product, monopentadecylpoly(2–3 moles in total)oxyethyloxypropylated product, monohexadecylpoly(2–3 moles in total)oxyethyloxypropylated product, monooctadecylpoly(2–3 moles in total)oxyethyloxypropylated product, mono(9-octadecenyl)poly(2–3 moles in total)oxyethyloxypropylated product, monoeicosylpoly(2–3 moles in total)oxyethyloxypropylated product, monodocosylpoly(2–3 moles)oxyethyloxypropylated product, monobutylphenylpoly(2–3 moles in total)oxyethyloxypropylated product, monooctylphenylpoly(2–3 moles in total)oxyethyloxypropylated product, and monononylphenylpoly(2–3 moles in total)oxyethyloxypropylated product. Among monohydroxyalkylalkylenediamines, there may be cited monohydroxyethylethylenediamine, monohydroxyethyl1,3-propylenediamine, monohydroxypropylethylenediamine and monohydroxypropyl-1,3-propylenediamine. As for the acetoacetic esters, on the other hand, mention may be made of methyl acetoacetate, ethyl acetoacetate, propyl acetoacetate, isopropyl acetoacetate and butyl acetoacetate. As for the formylpropionic esters, there may be cited methyl, ethyl, propyl and butyl esters of 2-formylpropionic acid, 3-formylpropionic acid, 2-formyl-2-methylpropionic acid and 3-formyl-2-methylpropionic acid. Among carboxylic acids, mention may be made of octylic acid, lauric acid, myristic acid, palmitic acid, stearic acid, oleic acid, linolic acid, 12-hydroxystearic acid, ricinolic acid and behenic acid. As for the monohalogenated carboxylic acids, there may be cited monochloroacetic acid, monobromoacetic acid, and monochloropropionic acid.

In producing the antibacterial surface active compound of this invention, the reaction between an acetoacetic ester or formylpropionic ester and a monoamide prepared from a carboxylic acid and a polyalkylenepolyamine, N-alkylpolyalkylenepolyamine, N-alkoxyalkylpolyalkylenepolyamine, monohydroxyalkylalkylenediamine or polyalkylenepolyamine is allowed to proceed by removing water or an alcohol under reduced pressure or atmospheric pressure at 50° to 250° C., preferably 100° to 180° C., thus leading to the N-alkylazaalkenylactam of this invention. In this case, neither a catalyst nor a solvent is particularly needed, while bubbling of an inert gas such as nitrogen or carbon dioxide is effective in accelerating the reaction. The reaction between an N-alkylazaalkenelactam and a monohalogenated carboxylic acid is allowed to proceed by bringing both into contact with each other at 30° to 100° C., preferably 50° to 80° C. in a polar solvent such as water, an alcohol, dioxane or tetrahydrofuran in the presence of a water-soluble inorganic alkali such as sodium hydroxide or potassium hydroxide. On the other hand, the reaction between an N-alkylazaalkenelactam and a salt of monohalogenated carboxylic acid proceeds simply on being contacted with each other at 30° to 100° C., preferably 50° to 80° C. in the presence of the above-noted polar solvent, leading to the compound of this invention. Further, the reaction between a carboxylic acid and a polyalkylenepolyamine or a reaction product of a polyalkylenepolyamine and an acetoacetic ester or formylpropionic ester, and the reaction between a carboxylic acid and a reaction product of a monohydroxyalkylalkylenediamine and an acetoacetic ester or formylpropionic ester proceed, similarly to wellknown amide formations and esterifications, by the dehydration under a reduced pressure or atmospheric pressure at 50° to 250° C., preferably 120° to 200° C. In these cases also neither a catalyst nor a reaction solvent is particularly needed, while the bubbling of an inert gas such as nitrogen or carbon dioxide makes easier the completion of the reaction.

BRIEF DESCRIPTION OF DRAWINGS

FIG. 2 is the diagram of IR spectrum of 4-dodecyl-7-methyl-1-azonia-4-azacyclohept-7-en-5-one-1-acetate which is the final product in Example 1. (5) represents the absorption band of

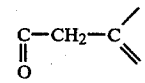

and (6) represents that of $\nu_{C=N^+}$.

Figure 1:
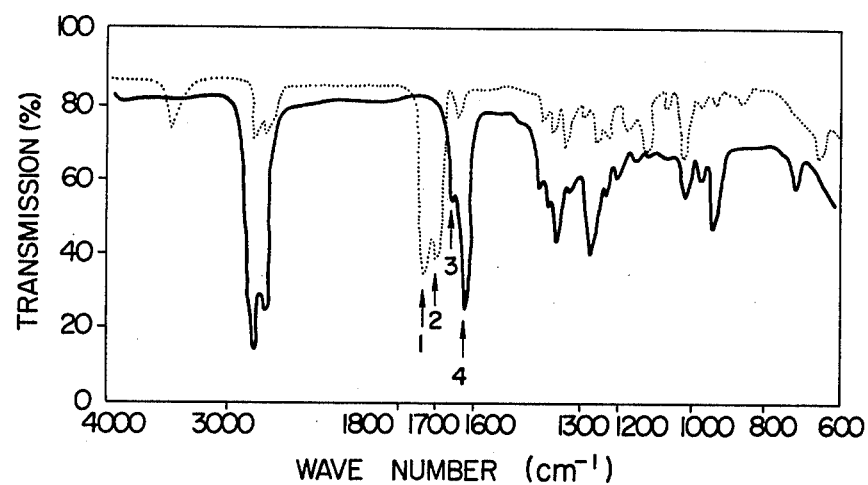
FIG. 1 is a diagrams of IR spectra of 4-dodecyl-7-methyl-3,6-dihydro-2H-1,4-diazepin-5-one (solid line) and its starting material ethyl acetoacetate (dotted line), respectively. (1) represents the absorption band of $\nu_{C=O}$ (ester), (2) that of $\nu_{C=O}$ (ketone), (3) that of $\nu_{C=O}$ (amide) and (4) that of $\nu_{C=N}$.
Figure 2:
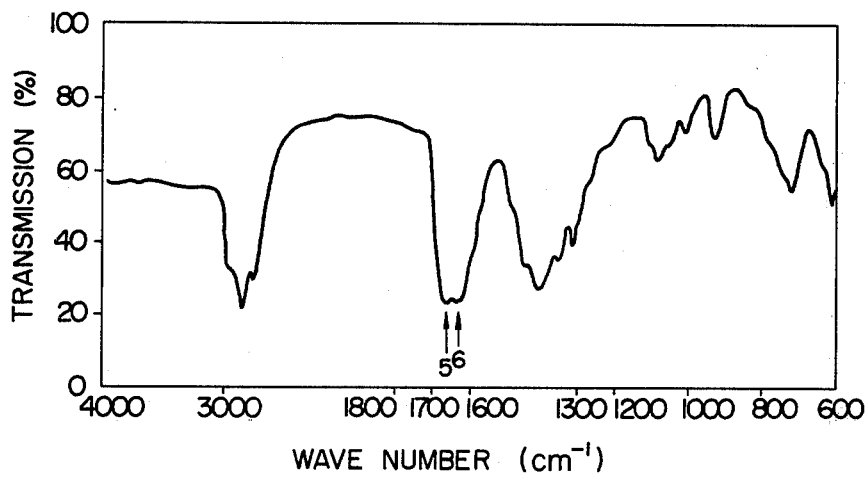
Figure 3:
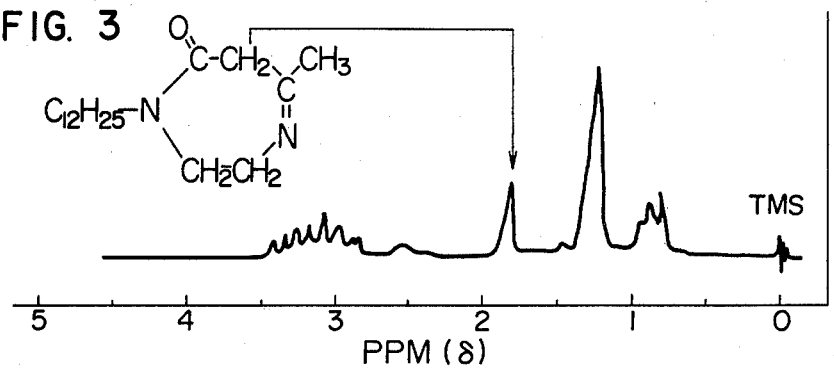
Figure 4:
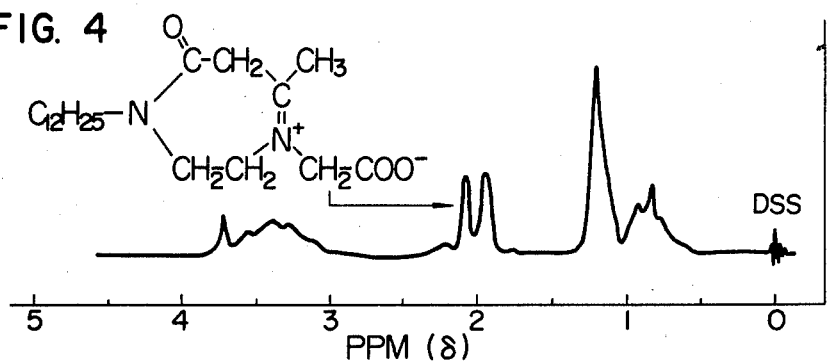

FIG. 3* and 4** are diagrams of 1H-NMR spectra of 4-dodecyl-7-methyl-3,6-dihydro-2H-1,4-diazepin-5-one and 4-dodecyl-7-methyl-1-azonia-4-azacyclohept-7-en-5-one-1-acetate, respectively.
(*TMS stands for tetramethylsilane and **DSS stands for sodium 2,2-dimethyl-2-silapentanesulfonate.)

Figure 5:
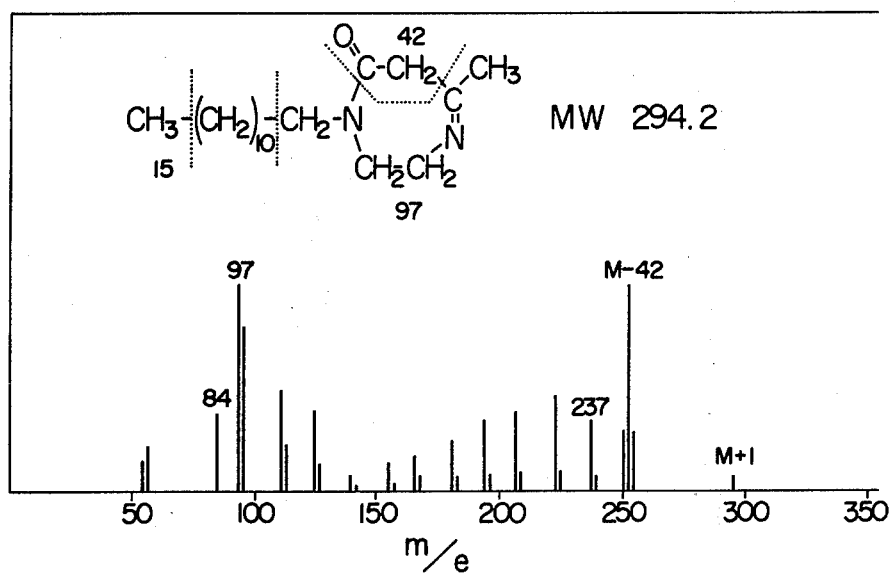

FIG. 5 is the diagram of mass spectrum of 4-dodecyl-7-methyl-3-methyl-3,6-dihydro-2H-1,4-diazepin-5-one.

Further, since the N-alkylazaalkenelactams and their derivatives having an organic acid radical, e.g. a carboxylate, which are the antibacterial surface active compounds containing a cyclic amide according to this invention, exhibit, even in a small amount, antibacterial activity against aerobic bacteria, anaerobic bacteria, gram-positive bacteria and gram-negative bacteria, they act as bactericides on man, animals, and environment. Even more, they act as an inhibitor for the bacterial corrosion of metals. Also, they themselves form a coating film on various metals to inhibit corrosion. Thus, these compounds are used as bactericides by themselves or, if necessary, in admixtures with various diluents.

BEST MODES FOR CARRYING OUT THE INVENTION

Examples are described below.

EXAMPLE 1

Into a four-necked flask provided with a stirrer, thermometer, gas inlet tube, and water measuring tube connected with a reflux condenser, were charged 228.1 g (1 mole) of N-dodecylethylenediamine and 130.1 g (1 mole) of ethyl acetoacetate. While bubbling nitrogen gas, the flask was heated at 150° to 160° C. to distill off 18 g of water and 46 g of ethanol, and then 4-dodecyl-7-methyl-3,6-dihydro-2H-1,4-diazepin-5-one in slight yellow liquid was obtained.

Elementary analysis: $C_{18}H_{34}ON_2$; Calculated (%)—C 73.48, H 11.64, N 9.52, Found (%)—C 73.50, H 11.65, N 9.55.

Amine value—192.0 (theoretical 190.8).

IR spectrum—1615 cm$^{-1}$ ($\nu_{C=N}$), 1660 cm$^{-1}$. ($\nu_{C=O}$, amide).

NMR spectrum—

proton 1.76 ppm (δ, TMS standard, 50 MHz).

Mass spectrum—(M+1) peak 295.

Subsequently, to a four-necked flask provided with a stirrer, thermometer, dropping funnel and an adapter for connecting with a reflux condenser, were charged 116.5 g (1 mole) of sodium monochloroacetate and 600 g of water to form a homogeneous solution. To the solution at 60° to 70° C., was added dropwise 294.2 g (1 mole) of 4-dodecyl-7-methyl-3,6-dihydro-2H-1,4-diazepin-5-one to perform acetate radical formation at the same temperature and to synthesize water-soluble 4-dodecyl-7-methyl-1-azonia-4-azacyclohept-7-en-5-on-1-acetate.

Elementary analysis: $C_{20}H_{36}O_3N_2$; Calculated (%)—C 68.20, H 10.30, N 7.95, Found (%)—C 68.18, H 10.32, N 7.96.

IR spectrum—1640 cm$^{-1}$

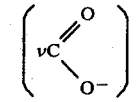

NMR spectrum—$N^+$-$CH_2COO^-$ proton 2.06 ppm (δ, DSS standard, 50 MHz).

EXAMPLE 2

Into an apparatus similar to that in Example 1, were charged 271.1 g (1 mole) of N-dodecyldiethylenetriamine and 116.1 g (1 mole) of methyl acetoacetate. After 18 g of water and 32 g of methanol had been distilled off at 140° to 150° C., there was obtained 4-dodecylaminoethyl-7-methyl-3,6-dihydro-2H-1,4-diazepin-5-one in slight red liquid.

Elementary analysis: $C_{20}H_{39}ON_3$; Calculated (%)—C 71.23, H 11.66, N 12.45, Found (%)—C 71.26, H 11.69, N 12.44.

Amine value—333.1 (theoretical 332.8).

IR spectrum—1615 cm$^{-1}$ ($\nu_{C=N}$), 1650 cm$^{-1}$ ($\nu_{C=O}$, amide).

NMR spectrum—

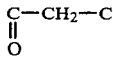

proton 1.78 ppm (δ, TMS standard, 50 MHz).

Mass spectrum (M+1) peak 338.

Subsequently, into a solution of 116.5 g (1 mole) of sodium monochloroacetate dissolved in 675 g of water, was added dropwise 337.2 g (1 mole) of 4-dodecylaminoethyl-7-methyl-3,6-dihydro-2H-1,4-diazepin-5-one to perform acetate radical formation at 50° to 60° C. and to synthesize 4-dodecylaminoethyl-7-methyl-1-azonia-4-azacyclohept-7-en-5-one-1-acetate.

Elementary analysis: $C_{22}H_{41}O_3N_3$; Calculated (%)—C 66.86, H 10.46, N 10.63, Found (%)—C 66.83, H 10.45, N 10.67.

IR spectrum—1635 cm$^{-1}$

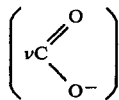

NMR spectrum—N$^+$-CH$_2$COO$^-$ proton 2.09 ppm (δ, DSS standard, 50 MHz).

EXAMPLE 3

Into an apparatus similar to that in Example 1, were charged 242.1 g (1 mole) of N-dodecyl-1,3-propylenediamine and 130.1 g (1 mole) of ethyl acetoacetate. At 150° to 160° C., 18 g of water and 46 g of ethanol were distilled off to obtain 1-dodecyl-4-methyl-3,6,7,8-tetrahydro-1,5-diazocin-2-one.

Elementary analysis: $C_{19}H_{36}ON_2$; Calculated (%)—C 74.04; H 11.77, N 9.09, Found (%)—C 74.04, H 11.79, N 9.08.

Amine value—181.9 (theoretical 182.1)

IR spectrum—1610 cm$^{-1}$ ($\nu_{C=N}$), 1660 cm$^{-1}$ ($\nu_{C=O}$, amide).

NMR spectrum—

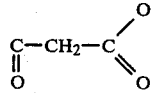

proton, 1.80 ppm (δ, TMS standard, 50 MHz).

Mass spectrum—(M+1) peak 309.

Subsequently, to a solution of 116.5 g (1 mole) of sodium monochloroacetate dissolved in 620 g of water, was added dropwise 308.2 g (1 mole) of 1-dodecyl-4-methyl-3,6,7,8-tetrahydro-1,5-diazocin-2-one to perform acetate radical formation as 60° to 70° C. and to synthesize 1-dodecyl-4-methyl-1-aza-5-azoniacyclooct-4-en-2-one-5-acetate.

Elementary analysis: $C_{21}H_{38}O_3N_2$; Calculated (%)—C 68.67, H 10.46, N 7.65, Found (%)—C 68.66, H 10.48, N 7.64.

IR spectrum—1635 cm$^{-1}$

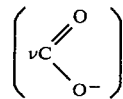

NMR spectrum—N$^+$-CH$_2$COO$^-$ proton 2.09 ppm (δ, DSS standard, 50 MHz).

EXAMPLE 4

Into an apparatus similar to that in Example 1, were charged 324.1 g (1 mole) of N-(9-octadecenyl)-1,3-propylenediamine and 130.1 g (1 mole) of ethyl acetoacetate. At 110° to 120° C. and under a reduced pressure of 50 mmHg, 18 g of water and 46 g of ethanol had been distilled off to obtain 1-(9-octadecenyl)-4-methyl-3,6,7,8-tetrahydro-1,5-diazocin-2-one.

Elementary analysis: $C_{25}H_{46}ON_2$; Calculated (%)—C 76.95, H 11.88, N 7.18, Found (%)—C 76.93, H 11.89, N 7.17.

Amine value—145.0 (theoretical 143.8)

IR spectrum—1610 cm$^{-1}$ ($\nu_{C=N}$), 1650 cm$^{-1}$ ($\nu_{C=O}$, amide).

Subsequently, to a solution of 116.5 g (1 mole) of sodium monochloroacetate dissolved in 700 g of water, was added dropwise 390.2 g (1 mole) of 1-(9-octadecenyl)-4-methyl-3,6,7,8-tetrahydro-1,5-diazocin-2-one. The acetate radical formation was effected at 70° to 80° C. to synthesize 1-(9-octadecenyl)-4-methyl-1-aza-5-azoniacyclooct-4-en-2-one-5-acetate.

Elementary analysis: $C_{27}H_{48}O_3N_2$; Calculated (%)—C 72.35, H 10.80, N 6.25, Found (%)—C 72.34, H 10.79, N 6.26.

IR spectrum—1635 cm$^{-1}$

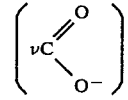

NMR spectrum—N$^+$-CH$_2$COO$^-$ proton 2.07 ppm (δ, DSS standard, 50 MHz).

EXAMPLE 5

Into an apparatus similar to that in Example 1, were charged 284.1 g (1 mole) of N-hexadecylethylenediamine and 130.1 g (1 mole) of ethyl acetoacetate. At 160° to 170° C., 18 g of water and 46 g of ethanol were distilled off to obtain 4-hexadecyl-7-methyl-3,6-dihydro-2H-1,4-diazepin-5-one.

Elementary analysis: $C_{22}H_{42}ON_2$; Calculated (%)—C 75.45, H 12.09, N 8.00, Found (%)—C 75.48, H 12.11, N 7.99.

Amine value—161.1 (theoretical 160.3).

IR spectrum—1615 cm$^{-1}$ ($\nu_{C=N}$), 1660 cm$^{-1}$ ($\nu_{C=O}$, amide).

Subsequently, into a solution of 116.5 g (1 mole) of sodium monochloroacetate dissolved in 600 g of water, was added dropwise 350.2 g (1 mole) of 4-hexadecyl-7-methyl-3,6-dihydro-2H-1,4-diazepin-5-one dissolved in 350 g of dioxane. The acetate radical formation was effected at 80° to 85° C. to synthesize 4-hexadecyl-7-methyl-1-azonia-4-azacyclohept-7-en-5-one-1-acetate.

Elementary analysis: $C_{24}H_{44}O_3N_2$; Calculated (%)—C 70.61, H 10.86, N 6.86, Found (%)—C 70.64, H 10.86, N 6.88.

IR spectrum—1640 cm$^{-1}$

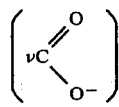

NMR spectrum—N+-CH₂COO⁻ proton 2.09 ppm (δ, DSS standard, 50 MHz).

EXAMPLE 6

Into an apparatus similar to that in Example 1, were charged 315.1 g (1 mole) of N-dodecoxyethyldiethylenetriamine and 130.1 g (1 mole) of ethyl acetoacetate at 150° to 160° C., 18 g of water and 46 g of ethanol were distilled off to obtain 4-dodecoxyethylaminoethyl-7-methyl-3,6-dihydro-2H-1,4-diazepin-5-one.

Elementary analysis: $C_{22}H_{43}O_2N_3$; Calculated (%)—C 69.31, H 11.37, N 11.02, Found (%)—C 69.29, H 11.39, N 10.98.

Amine value—296.1 (theoretical 294.4).

IR spectrum—1615 cm⁻¹ ($\nu_{C=N}$), 1660 cm⁻¹ ($\nu_{C=O}$, amide).

Subsequently, into a solution of 116.5 g (1 mole) of sodium monochloroacetate dissolved in 700 g of water, was added dropwise 381.2 g (1 mole) of 4-dodecoxyethylaminoethyl-7-methyl-3,6-dihydro-2H-1,4-diazepin-5-one. The acetate radical formation was effected at 60° to 70° C. to synthesize 4-dodecoxyaminoethyl-7-methyl-1-azonia-4-azacyclohept-7-en-5-one-1-acetate.

Elementary analysis: $C_{24}H_{45}O_4N_3$; Calculated (%)—C 65.63, H 10.33, N 9.56, Found (%)—C 65.68, H 10.30, N 9.58.

IR spectrum—1640 cm⁻¹

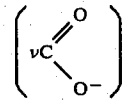

NMR spectrum—N+-CH₂COO⁻ proton 2.09 ppm (δ, DSS standard, 50 MHz).

EXAMPLE 7

Into an apparatus similar to that in Example 1, were charged 364.2 g (1 mole) of N-nonylphenylpoly(2 moles)oxyethyleneoxyethyl-1,3-propylenediamine and 130.1 g (1 mole) of ethyl acetoacetate. At 110° to 120° C. and under a reduced pressure of 50 mmHg, 18 g of water and 46 g of ethanol were distilled off to obtain 1-nonylphenylpoly(2 moles)oxyethyleneoxyethyl-4-methyl-3,6,7,8-tetrahydro-1,5-diazocin-2-one.

Elementary analysis: $C_{26}H_{42}O_3N_2$; Calculated (%)—C 72.57, H 9.84, N 6.51, Found (%)—C 72.55, H 9.87, N 6.48.

Amine value—128.2 (theoretical 130.4).

IR spectrum—1620 cm⁻¹ ($\nu_{C=N}$), 1650 cm⁻¹ ($\nu_{C=O}$, amide).

Subsequently, into a solution of 161.0 g (1 mole) of sodium monobromoacetate dissolved in 500 g of water, was added dropwise 430.3 g (1 mole) of 1-nonylphenylpoly(2 moles)oxyethyleneoxyethyl-4-methyl-3,6,7,8-tetrahydro-1,5-diazocin-2-one dissolved in 300 g of tetrahydrofuran. The acetate radical formation was effected at 80° to 85° C. to synthesize 1-nonylphenylpoly(2 moles)oxyethyleneoxyethyl-4-methyl-1-aza-5-azoniacyclooct-4-en-2-one-5-acetate.

Elementary analysis: $C_{28}H_{44}O_5N_2$; Calculated (%)—C 68.87, H 9.08, N 5.73, Found (%)—C 68.85, H 9.09, N 5.77.

IR spectrum—1635 cm⁻¹

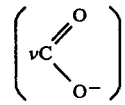

NMR spectrum—N+-CH₂COO⁻ proton 2.10 ppm (δ, DSS standard, 50 MHz).

EXAMPLE 8

Into an apparatus similar to that in Example 1, were charged 230.1 g (1 mole) of N-octoxypropylethylenediamine and 116.1 g (1 mole) of methyl acetoacetate. At 140° to 145° C., 18 g of water and 32 g of ethanol were distilled off to obtain 4-octoxypropyl-7-methyl-3,6-dihydro-2H-1,4-diazepin-5-one.

Elementary analysis: $C_{17}H_{32}O_2N_2$; Calculated (%)—C 68.93, H 10.89, N 9.45, Found (%)—C 68.91, H 10.90, N 9.45.

Amine value—190.0 (theoretical 189.4).

IR spectrum—1610 cm⁻¹ ($\nu_{C=N}$), 1655 cm⁻¹ ($\nu_{C=O}$, amide).

Subsequently, to a solution of 132.6 g (1 mole) of potassium monochloroacetate dissolved in 600 g of water, was added dropwise 296.2 g (1 mole) of 4-octoxypropyl-7-methyl-3,6-dihydro-2H-1,4-diazepin-5-one. The acetate radical formation was effected at 50° to 60° C. to synthesize 4-octoxypropyl-7-methyl-1-azonia-4-azacyclohept-7-en-5-one-1-acetate.

Elementary analysis: $C_{19}H_{34}O_4N_2$; Calculated (%)—C 64.42, H 9.68, N 7.91, Found (%)—C 64.46, H 9.66, N 7.89.

IR spectrum—1635 cm⁻¹

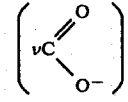

NMR spectrum—N+-CH₂COO⁻ proton 2.17 ppm (δ, DSS standard, 50 MHz).

EXAMPLE 9

Into an apparatus similar to that in Example 1, were charged 103.1 g (1 mole) of diethylenetriamine and 116.1 g (1 mole) of methyl acetoacetate. At 140° to 150° C., 18 g of water and 32 g of methanol were distilled off. Then, with the addition of 200.3 g (1 mole) of lauric acid, the amide formation was effected at 200° to 210° C. and 18 g of water was distilled off, leaving behind 4-lauramidoethyl-7-methyl-3,6-dihydro-2H-1,4-diazepin-5-one.

Elementary analysis: $C_{20}H_{37}O_2N_3$; Calculated (%)—C 68.37, H 10.62, N 11.96, Found (%)—C 68.37, H 10.60, N 11.95.

Amine value—161.3 (theoretical 159.7).

IR spectrum—1610 cm⁻¹ ($\nu_{C=N}$), 1660 cm⁻¹ ($\nu_{C=O}$, amide).

Subsequently, to a solution of 116.5 g (1 mole) of sodium monochloroacetate dissolved in 400 g of water, was added dropwise 351.3 g (1 mole) of 4-lauramidoethyl-7-methyl-3,6-dihydro-2H-1,4-diazepin-5-one dissolved in 350 g of methanol. The acetate radical formation was effected at 55° to 60° C. to synthesize 4-lauramidoethyl-7-methyl-1-azonia-4-azacyclohept-7-en-5-one-1-acetate.

Elementary analysis: $C_{22}H_{39}O_4N_3$; Calculated (%)—C 64.55, H 9.60, N 10.26, Found (%)—C 64.58, H 9.58, N 10.23.

IR spectrum—1640 cm$^{-1}$

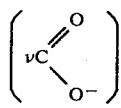

NMR spectrum N$^+$-CH$_2$COO$^-$ proton 2.03 ppm (δ, DSS standard, 50 MHz).

EXAMPLE 10

Into an apparatus similar to that in Example 1, were charged 103.1 g (1 mole) of diethylenetriamine and 116.1 g (1 mole) of methyl acetoacetate. At 110° to 120° C. and under a reduced pressure of 70 mmHg, 18 g of water and 32 g of methanol were distilled off. Then, with the addition of 282.5 g (1 mole) of oleic acid, the amide formation was effected at 210° to 215° C. to distil off 18 g of water and to obtain 4-oleamidoethyl-7-methyl-3,6-dihydro-2H-1,4-diazepin-5-one.

Elementary analysis: $C_{26}H_{47}O_2N_3$; Calculated (%)—C 72.07, H 10.93, N 9.69, Found (%)—C 72.04, H 10.97, N 9.66.

Amine value—131.0 (theoretical 129.6).

IR spectrum—1610 cm$^{-1}$ ($\nu_{C=N}$), 1650 cm$^{-1}$ ($\nu_{C=O}$, amide).

Subsequently, to a solution of 161.0 g (1 mole) of sodium monobromoacetate dissolved in 800 g of water, was added dropwise 433.3 g (1 mole) of 4-oleamidoethyl-7-methyl-3,6-dihydro-2H-1,4-diazepin-5-one. The acetate radical formation was effected at 70° to 80° C. to synthesize 4-oleamidoethyl-7-methyl-1-azonia-4-azacyclohept-7-en-5-one-1-acetate.

Elementary analysis: $C_{28}H_{49}O_4N_3$; Calculated (%)—C 68.45, H 10.05, N 8.55, Found (%)—C 68.44, H 10.01, N 8.58.

IR spectrum—1635 cm$^{-1}$

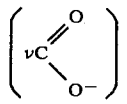

NMR spectrum—N$^+$-CH$_2$COO$^-$ proton 2.11 ppm (δ, DSS standard, 50 MHz).

EXAMPLE 11

Into an apparatus similar to that in Example 1, were charged 103.1 g (1 mole) of diethylenetriamine and 284.5 g (1 mole) of isostearic acid. At 200° to 210° C., 18 g of water was distilled off to effect the monoamide formation. Then, after the addition of 130.1 g (1 mole) of ethyl acetoacetate, 18 g of water and 46 g of ethanol were distilled off at 150° to 160° C. to obtain 4-isostearamidoethyl-7-methyl-3,6-dihydro-2H-1,4-diazepin-5-one.

Elementary analysis: $C_{26}H_{49}O_2N_3$; Calculated (%)—C 71.73, H 11.35, N 9.65, Found (%)—C 71.75, H 11.33, N 9.65.

Amine value—127.1 (theoretical 128.9).

IR spectrum—1615 cm$^{-1}$ ($\nu_{C=N}$), 1660 cm$^{-1}$ ($\nu_{C=O}$, amide).

Subsequently, to a solution of 116.5 g of sodium monochloroacetate dissolved in 800 g of water, was added dropwise 435.3 g (1 mole) of 4-isostearamidoethyl-7-methyl-3,6-dihydro-2H-1,4-diazepin-5-one. The acetate radical formation was effected at 70° to 80° C. to synthesize 4-isostearamidoethyl-7-methyl-1-azonia-4-azacyclohept-7-en-5-one-1-acetate.

Elementary analysis: $C_{28}H_{51}O_4N_3$; Calculated (%)—C 68.17, H 10.42, N 8.51, Found (%)—C 68.20, H 10.42, N 8.49.

IR spectrum—1630 cm$^{-1}$

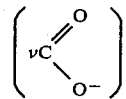

NMR spectrum—N$^+$-CH$_2$COO$^-$ proton 2.05 ppm (δ, DSS standard, 50 MHz).

EXAMPLE 12

Into an apparatus similar to that in Example 1, were charged 104.2 g (1 mole) of N-hydroxyethylethylenediamine and 130.1 g (1 mole) of ethyl acetoacetate. At 150° to 160° C., 18 g of water and 46 g of ethanol were distilled off. Then, after addition of 200.3 g (1 mole) of lauric acid, the esterification was effected at 200° to 210° C. to distil off 18 g of water and to obtain 4-lauroyloxyethyl-7-methyl-3,6-dihydro-2H-1,4-diazepin-5-one.

Elementary analysis: $C_{20}H_{36}O_3N_2$; Calculated (%)—C 68.12, H 10.29, N 7.94, Found (%)—C 68.15, H 10.27, N 7.96.

Amine value—161.2 (theoretical 159.1).

IR spectrum—1610 cm$^{-1}$ ($\nu_{C=N}$), 1650 cm$^{-1}$ ($\nu_{C=O}$, amide), 1740 cm$^{-1}$ ($\nu_{C=O}$, ester).

Subsequently, into a solution of 116.5 g (1 mole) of sodium monochloroacetate dissolved in 800 g of water, was added dropwise 352.6 g (1 mole) of 4-lauroyloxyethyl-7-methyl-3,6-dihydro-2H-1,4-diazepin-5-one. The acetate radical formation was effected at 55° to 65° C. to synthesize 4-lauroyloxyethyl-7-methyl-1-azonia-4-azacyclohept-7-en-5-one-1-acetate.

Elementary analysis: $C_{22}H_{38}O_5N_2$; Calculated (%)—C 64.35, H 9.33, N 6.82, Found (%)—C 64.31, H 9.35, N 6.79.

IR spectrum—1635 cm$^{-1}$

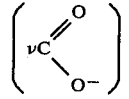

NMR spectrum—N$^+$-CH$_2$COO$^-$ proton 2.08 ppm (δ, DSS standard, 50 MHz).

EXAMPLE 13

Into an apparatus similar to that in Example 1, were charged 104.2 g (1 mole) of N-hydroxyethylethylenediamine and 130.1 g (1 mole) of ethylacetoacetate. At 150° to 160° C., 18 g of water and 46 g of ethanol were distilled off. Then, after addition of 282.5 g (1 mole) of oleic acid, the esterification was effected at 210° to 215° C. to distil off 18 g of water and to obtain 4-oleoyloxyethyl-7-methyl-3,6-dihydro-2H-1,4-diazepin-5-one.

Elementary analysis: $C_{26}H_{46}O_3N_2$; Calculated (%)—C 71.83, H 10.67, N 6.44, Found (%)—C 71.85, H 10.69, N 6.44.

Amine value—130.6 (theoretical 129.1).

IR spectrum—1610 cm$^{-1}$ ($\nu_{C=N}$), 1650 cm$^{-1}$ ($\nu_{C=O}$, amide) 1740 cm$^{-1}$ ($\nu_{C=O}$, ester).

Subsequently, to a solution of 434.7 g (1 mole) of 4-oleoyloxyethyl-7-methyl-3,6-dihydro-2H-1,4-diazepin-5-one dissolved in 400 g of isopropyl alcohol, was added dropwise an aqueous solution of 116.5 g (1 mole) of sodium monochloroacetate dissolved in 500 g of water. The acetate radical formation was effected at 60° to 70° C. to synthesize 4-oleoyloxyethyl-7-methyl-1-azonia-4-azacyclohept-7-en-5-one-1-acetate.

Elementary analysis: $C_{28}H_{48}O_5N_2$; Calculated (%)—C 68.25, H 9.82, N 5.68, Found (%)—C 68.21, H 9.80, N 5.69.

IR spectrum—1630 cm$^{-1}$

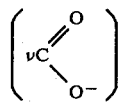

NMR spectrum—N$^+$-CH$_2$COO$^-$ proton 2.08 ppm (δ, DSS standard, 50 MHz).

EXAMPLE 14

Into an apparatus similar to that in Example 1, were charged 118.2 g (1 mole) of N-hydroxyethyl-1,3-propylenediamine and 116.1 g (1 mole) of methyl acetoacetate. At 115° to 120° C. and under a reduced pressure of 100 mmHg, 18 g of water and 32 g of methanol were distilled off. Then, after addition of 200.3 g (1 mole) of lauric acid, the esterification was effected at 190° to 200° C. to distil off 18 g of water and to obtain 1-lauroyloxyethyl-4-methyl-3,6,7,8-tetrahydro-1,5-diazocin-2-one.

Elementary analysis: $C_{21}H_{38}O_3N_2$; Calculated (%)—C 68.82, H 10.45, N 7.64, Found (%)—C 68.79, H 10.47, N 7.66.

Amine value—153.0 (theoretical 153.1).

IR spectrum—1615 cm$^{-1}$ ($\nu_{C=N}$), 1660 cm$^{-1}$ ($\nu_{C=O}$, amide), 1735 cm$^{-1}$ ($\nu_{C=O}$, ester).

Subsequently, to a solution of 177.0 g (1 mole) of potassium monobromoacetate dissolved in 800 g of water, was added dropwise 366.5 g (1 mole) of 1-lauroyloxyethyl-4-methyl-3,6,7,8-tetrahydro-1,5-diazocin-2-one. The acetate radical formation was effected at 55° to 65° C. to synthesize 1-lauroyloxyethyl-4-methyl-1-aza-5-azoniacyclooct-4-en-2-one-5-acetate.

Elementary analysis: $C_{23}H_{40}O_5N_2$; Calculated (%)—C 65.07, H 9.50, N 6.60, Found (%)—C 65.10, H 9.49, N 6.60.

IR spectrum—1635 cm$^{-1}$

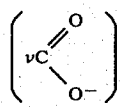

NMR spectrum—N$^+$-CH$_2$COO$^-$ proton 2.07 ppm (δ, DSS standard, 50 MHz).

EXAMPLE 15

Into an apparatus similar to that in Example 1, were charged 256.1 g (1 mole) of N-coconutalkyl-1,3-propylenediamine (wherein, the carbon number composition is 5% C$_8$, 10% C$_{10}$, 50% C$_{12}$, 20% C$_{14}$, 10% C$_{16}$ and 5% C$_{18}$) and 116.1 g (1 mole) of methyl acetoacetate. At 145° to 155° C., 18 g of water and 32 g of methanol were distilled off to obtain 1-coconutalkyl-4-methyl-3,6,7,8-tetrahydro-1,5-diazocin-2-one.

Elementary analysis: $C_{20}H_{38}ON_2$; Calculated (%)—C 74.48, H 11.88, N 8.68, Found (%)—C 74.51, H 11.90, N 8.65.

Amine value—175.1 (theoretical 174.0).

IR spectrum—1620 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 850 g of water, was added dropwise 322.5 g (1 mole) of 1-coconutalkyl-4-methyl-3,6,7,8-tetrahydro-1,5-diazocin-2-one. The acetate radical formation was effected at 70° to 80° C. to synthesize 1-coconutalkyl-4-methyl-1-aza-5-azoniacyclooct-4-en-2-one-5-acetate.

Elementary analysis: $C_{22}H_{40}O_3N_2$; Calculated (%)—C 69.44, H 10.60, N 7.36, Found (%)—C 69.40, H 10.59, N 7.39.

IR spectrum—1635 cm$^{-1}$

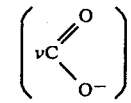

NMR spectrum—N$^+$-CH$_2$COO$^-$ proton 2.09 ppm (δ, DSS standard, 50 MHz).

EXAMPLE 16

Into an apparatus similar to that in Example 1, were charged 301.5 g (1 mole) of monooctylated 1,3-propylenediamine-poly(3 moles on the average)ethyleneimine adduct and 158.1 g (1 mole) of butyl acetoacetate. At 150° to 160° C. and under a reduced pressure of 50 mmHg, 18 g of water and 74 g of butanol were distilled off to synthesize N-alkylalkenelactam.

Elementary analysis: $C_{21}H_{42}ON_5$; Calculated (%)—C 66.23, H 11.12, N 18.38, Found (%)—C 66.23, H 11.10, N 18.41.

Amine value—592.1 (theoretical 589.4).

IR spectrum—1610 cm$^{-1}$ ($\nu_{C=N}$), 1650 cm$^{-1}$ ($\nu_{C=O}$, amide).

Subsequently, to a solution of 94.5 g (1 mole) of monochloroacetic acid dissolved in 450 g of water, was added dropwise 380.8 g of N-alkylalkenelactam obtained above. After mixing at 60° to 70° C. and further adding 40.0 g (1 mole) of sodium hydroxide, the reaction was allowed to proceed at the same temperature to synthesize the compound having anacetate radical.

Elementary analysis: $C_{23}H_{44}O_3N_5$; Calculated (%)—C 62.95, H 10.11, N 15.95, Found (%)—C 62.96, H 10.01, N 15.97.

IR spectrum—1640 cm$^{-1}$

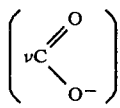

NMR spectrum—N+-CH₂COO⁻ proton 2.03 ppm (δ, DSS standard, 50 MHz).

EXAMPLE 17

Into an apparatus similar to that in Example 1, were charged 203.3 g (1 mole) of 1,3-propylenediamine-poly(3 moles on the average)ethyleneimine adduct and 300.5 g (1 mole) of 12-hydroxystearic acid. At 220° to 225° C., 18 g of water was distilled off to effect the monoamide formation. Then, 116.1 g (1 mole) of methyl acetoacetate was charged. At 110° to 115° C. and under a reduced pressure of 70 mm Hg, 18 g of water and 32 g of methanol were distilled off to synthesize N-alkylazaalkenelactam.

Elementary analysis: $C_{31}H_{61}O_3N_5$; Calculated (%)—C 67.47, H 11.14, N 12.69, Found (%)—C 67.46, H 11.12, N 12.71.

Amine value—306.1 (theoretical 305.0).

IR spectrum—1620 cm⁻¹ ($\nu_{C=N}$), 1655 cm⁻¹ ($\nu_{C=O}$, amide). Subsequently, a solution of 139.0 g (1 mole) of monobromoacetic acid dissolved in 800 g of water and a solution of 551.8 g (1 mole) of N-alkylazaalkenelactam dissolved in 500 g of tetrahydrofuran were mixed at 50° to 60° C. After addition of 40.0 g (1 mole) of sodium hydroxide, the reaction was allowed to proceed to form the compound having an acetate radical.

Elementary analysis: $C_{33}H_{63}O_5N_5$; Calculated (%)—C 64.99, H 10.42, N 11.48, Found (%)—C 64.96, H 10.42, N 11.45.

IR spectrum—1640 cm⁻¹

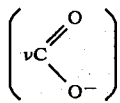

NMR spectrum—N+-CH₂COO⁻ proton 2.12 ppm (δ, DSS standard, 50 MHz).

EXAMPLE 18

Into an apparatus similar to that in Example 1, were charged 528.8 g of N-dodecylpoly(2 moles on the average)oxypropyleneoxypropylethylenediamine and 116.5 g (1 mole) of methyl acetoacetate. At 170° to 175° C., 18 g of water and 32 g of methanol were distilled off to synthesize N-alkylazaalkenelactam.

Elementary analysis: $C_{37}H_{72}O_4N_2$; Calculated (%)—C 72.97, H 11.92, N 4.60, Found (%)—C 73.00, H 11.88, N 4.62.

Amine value—92.0 (theoretical 92.1).

IR spectrum—1615 cm⁻¹ ($\nu_{C=N}$), 1660 cm⁻¹ ($\nu_{C=O}$, amide).

Subsequently, a solution of 94.5 g (1 mole) of monochloroacetic acid in 500 g of water and a solution of 609.0 g (1 mole) of the N-alkylazaalkenelactam in 600 g of dioxane were mixed at 70° to 80° C. After further addition of 56.1 g (1 mole) of potassium hydroxide, the reaction was allowed to proceed to form the compound having an acetate radical Elementary analysis: $C_{39}H_{74}O_6N_2$; Calculated (%)—C 70.22, H 11.18, N 4.20, Found (%)—C 72.20, H 11.22, N 4.17.

IR spectrum—1640 cm⁻¹

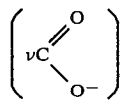

NMR spectrum—N+-CH₂COO⁻ proton 2.07 ppm (δ, DSS standard, 50 MHz).

EXAMPLE 19

Into an apparatus similar to that in Example 1, were charged 408.5 g (1 mole) of N-octylphenoxyethyleneoxypropyleneoxypropylethylenediamine and 116.5 g (1 mole) of methyl acetoacetate. At 170° to 175° C., 18 g of water and 32 g of methanol were distilled off to synthesize N-alkylazaalkenelactam.

Elementary analysis: $C_{28}H_{46}O_4N_2$; Calculated (%)—C 70.84, H 9.77, N 5.90, Found (%) C 70.80, H 9.75, N 5.90.

Amine value—117.7 (theoretical 118.2).

IR spectrum—1610 cm⁻¹ ($\nu_{C=N}$), 1655 cm⁻¹ ($\nu_{C=O}$, amide). Subsequently, a solution of 94.5 g (1 mole) of monochloroacetic acid dissolved in 500 g of water and a solution of 474.7 g (1 mole) of the formed N-alkylazaalkenelactam dissolved in 500 g of isopropyl alcohol were mixed at 65° to 75° C. After further addition of 40.0 g (1 mole) of sodium hydroxide, the reaction was allowed to proceed to form the compound having an acetate radical.

Elementary analysis: $C_{30}H_{48}O_6N_2$; Calculated (%)—C 67.63, H 9.08, N 5.26, Found (%)—C 67.60, H 9.08, N 5.23.

IR spectrum—1630 cm⁻¹

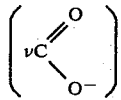

NMR spectrum—N+-CH₂COO⁻ proton 2.08 ppm (δ, DSS standard, 50 MHz).

EXAMPLE 20

Into an apparatus similar to that in Example 1, were charged 429.6 g (1 mole) of a monotridecoxyethyl derivative of 1,3-propylenediamine-poly(3 moles on the average)ethyleneimine adduct and 130.1 g (1 mole) of ethyl acetoacetate. At 165° to 170° C., 18 g of water and 46 g of ethanol were distilled off to synthesize N-alkylazaalkenelactam.

Elementary analysis: $C_{28}H_{57}O_2N_5$; Calculated (%)—C 67.83, H 11.59, N 14.12, Found (%)—C 67.86, H 11.60, N 14.10.

Amine value—454.0 (theoretical 452.7).

IR spectrum—1610 cm⁻¹ ($\nu_{C=N}$), 1650 cm⁻¹ ($\nu_{C=O}$, amide).

Subsequently, to a solution of 116.5 g (1 mole) of sodium monochloroacetate dissolved in 1,000 g of water, was added dropwise 495.8 (1 mole) of the formed N-alkylazaalkenelactam. The reaction was allowed to proceed at 60° to 70° C. to obtain the compound having an acetate radical.

Elementary analysis: $C_{30}H_{59}O_4N_5$; Calculated (%)—C 65.07, H 10.74, N 12.64, Found (%)—C 65.11, H 10.75, N 12.60.

IR spectrum—1635 cm$^{-1}$

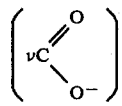

NMR spectrum—N$^+$-CH$_2$COO$^-$ proton 2.10 ppm (δ, DSS standard, 50 MHz).

EXAMPLE 21

Into an apparatus similar to that in Example 1, were charged 132.2 g (1 mole) of N-hydroxypropyl-1,3-propylenediamine and 116.1 g (1 mole) of methyl acetoacetate. At 140° to 150° C., 18 g of water and 32 g of methanol were distilled off. After addition of 298.5 g (1 mole) of ricinolic acid, the esterification was effect at 220° to 225° C. to distil off 18 g of water and to synthesize N-alkylazaalkenelactam.

Elementary analysis: $C_{28}H_{50}O_4N_2$; Calculated (%)—C 70.25, H 10.53, N 5.85, Found (%)—C 70.30, H 10.55, N 5.86.

Amine value—117.1 (theoretical 117.2).

IR spectrum—1615 cm$^{-1}$ ($\nu_{C=N}$), 1660 cm$^{-1}$ ($\nu_{C=O}$, amide), 1740 cm$^{-1}$ ($\nu_{C=O}$, ester).

Subsequently, to a solution of 116.5 g (1 mole) of sodium monochloroacetate dissolved in 1,000 g of water, was added dropwise 478.7 g (1 mole) of the formed N-alkylazaalkenelactam. The reaction was allowed to proceed at 60° to 70° C. to obtain the compound having an acetate radical.

Elementary analysis: $C_{30}H_{52}O_6N_2$; Calculated (%)—C 67.14, H 9.77, N 5.22, Found (%)—C 67.12, H 9.76, N 5.23.

IR spectrum—1640 cm$^{-1}$

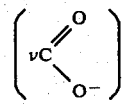

NMR spectrum—N$^+$-CH$_2$COO$^-$ proton 2.08 ppm (δ, DSS standard, 50 MHz).

EXAMPLE 22

In a manner similar to that in Example 1, at first 4-docosylaminoethyl-7-methyl-3,6-dihydro-2H-1,4-diazepin-5-one was synthesized using as starting materials 411.7 g (1 mole) of N-docosyldiethylenetriamine and 130.1 g (1 mole) of ethyl acetoacetate.

Elementary analysis: $C_{30}H_{59}ON_3$; Calculated (%)—C 75.40, H 12.45, N 8.79, Found (%)—C 75.38, H 12.46, N 8.82.

Amine value—234.0 (theoretical 234.9).

IR spectrum—1615 cm$^{-1}$ ($\nu_{C=N}$), 1660 cm$^{-1}$ ($\nu_{C=O}$, amide).

Then, 477.8 g (1 mole) of the formed 4-docosylaminoethyl-7-methyl-3,6-dihydro-2H-1,4-diazepin-5-one and 116.5 g (1 mole) of sodium monochloroacetate were allowed to react in the presence of 1,200 g of water to synthesize 4-docosylaminoethyl-7-methyl-1-azonia-4-azacyclohept-7-en-5-one-1-acetate.

Elementary analysis: $C_{32}H_{61}O_3N_3$; Calculated (%)—C 71.73, H 11.48, N 7.84, Found (%)—C 71.73, H 11.45, N 7.83.

IR spectrum—1635 cm$^{-1}$

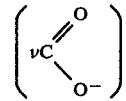

NMR spectrum—N$^+$-CH$_2$COO$^-$ proton 2.08 ppm (δ, DSS standard, 50 MHz).

EXAMPLE 23

In a manner similar to that in Example 9, using 103.1 g (1 mole) of diethylenetriamine 116.1 g (1 mole) of methyl acetoacetate, and 144.2 g (1 mole) of octylic acid as starting materials, at first 4-octamidoethyl-7-methyl-3,6-dihydro-2H-1,4-diazepin-5-one was synthesized.

Elementary analysis: $C_{16}H_{29}O_2N_3$; Calculated (%)—C 65.09, H 9.90, N 14.23, Found (%)—C 65.11, H 9.88, N 14.20.

Amine value—192.2 (theoretical 190.1).

IR spectrum—1620 cm$^{-1}$ ($\nu_{C=O}$), 1660 cm$^{-1}$ ($\nu_{C=O}$, amide).

Then, 295.2 g (1 mole) of the formed 4-octamidoethyl-7-methyl-3,6-dihydro-2H-1,4-diazepin-5-one and 116.5 g (1 mole) of sodium monochloroacetate were allowed to react in the presence of 600 g of water to synthesize 4-octamidoethyl-7-methyl-1-azonia-4-azacyclohept-7-en-5-one-1-acetate.

Elementary analysis: $C_{18}H_{31}O_4N_3$; Calculated (%)—C 61.21, H 8.85, N 11.89, Found (%)—C 61.18, H 8.83, N 11.90.

IR spectrum—1635 cm$^{-1}$

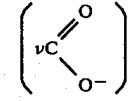

NMR spectrum—N$^+$-CH$_2$COO$^-$ proton 2.09 ppm (δ, DSS standard, 50 MHz).

EXAMPLE 24

In a manner similar to that in Example 12, using 104.2 g (1 mole) of N-hydroxyethylethylenediamine, 130.1 g (1 mole) of ethyl acetoacetate and 144.2 g (1 mole) of octylic acid as starting materials, at first 4-octoyloxyethyl-7-methyl-3,6-dihydro-2H-1,4-diazepin-5-one.

Elementary analysis: $C_{16}H_{28}O_3N_2$; Calculated (%)—C 64.83, H 9.52, N 9.45, Found (%)—C 64.80, H 9.49, N 9.43.

Amine value—190.8 (theoretical 189.3).

IR spectrum—1615 cm$^{-1}$ ($\nu_{C=N}$), 1660 cm$^{-1}$ ($\nu_{C=O}$, amide), 1740 cm$^{-1}$ ($\nu_{C=O}$, ester).

Then, 296.4 g (1 mole) of the formed 4-octoyloxyethyl-7-methyl-3,6-dihydro-2H-1,4-diazepin-5-one and 116.5 g (1 mole) of sodium monochloroacetate were allowed to react in the presence of 750 g of water to synthesize 4-octoyloxyethyl-7-methyl-1-azonia-4-azacyclohept-7-en-5-one-1-acetate.

Elementary analysis: $C_{18}H_{30}O_5N_2$; Calculated (%)—C 61.00, H 8.53, N 7.90, Found (%)—C 60.95, H 8.50, N 7.93.

IR spectrum—1635 cm$^{-1}$

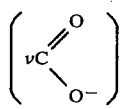

NMR spectrum—N+-CH₂COO⁻ proton 2.10 ppm (δ, DSS standard, 50 MHz).

EXAMPLE 25

In a manner similar to that in Example 12, using 132.2 g (1 mole) of N-hydroxypropyl-1,3-propylenediamine, 116.1 g (1 mole) of methyl acetoacetate, and 340.5 g (1 mole) of behenic acid as starting materials, at first 1-behenoyloxypropyl-4-methyl-3,6,7,8-tetrahydro-1,5-diazocin-2-one was synthesized.

Elementary analysis: $C_{32}H_{58}O_3N_2$; Calculated (%)—C 74.08, H 11.27, N 53.97, Found (%)—C 74.11, H 11.27, N 54.00.

Amine value—108.2 (theoretical 108.1).

IR spectrum—1615 cm⁻¹ ($v_{C=N}$), 1660 cm⁻¹ ($v_{C=O}$, amide), 1735 cm⁻¹ ($v_{C=O}$, ester).

Then, 518.8 g (1 mole) of 1-behenoyloxypropyl-4-methyl-3,6,7,8-tetrahydro-1,5-diazocin-2-one and 116.5 g (1 mole) of sodium monochloroacetate were allowed to react in the presence of 600 g of water and 600 g of isopropyl alcohol to synthesize 1-behenoyloxypropyl-4-methyl-1-aza-5-azoniacyclooct-4-en-2-one-5-acetate.

Elementary analysis: $C_{34}H_{60}O_5N_2$; Calculated (%)—C 70.79, H 10.49, N 4.85, Found (%)—C 70.81, H 10.51, N 4.84.

IR spectrum—1640 cm⁻¹

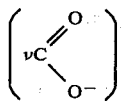

NMR spectrum—N+-CH₂COO⁻ proton 2.04 ppm (δ, DSS standard, 50 MHz).

EXAMPLE 26

Into an apparatus similar to that in Example 1, were charged 244.8 g (1 mole) of N-(2-hydroxy)dodecylethylenediamine and 116.1 g (1 mole) of methyl acetoacetate. At 140° to 150° C., 18 g of water and 32 g of methanol were distilled off to obtain white wax-like 4-(2-hydroxy)dodecyl-7-methyl-3,6-dihydro-2H-1,4-diazepin-5-one.

Elementary analysis: $C_{18}H_{34}O_2N_2$; Calculated (%)—C 69.56, H 11.03, N 9.01, Found (%)—C 69.39, H 11.06, N 9.07.

Amine value—180.6 (theoretical 180.5).

IR spectrum—1620 cm⁻¹ ($v_{C=N}$), 1660 cm⁻¹ ($v_{C=O}$, amide). Subsequently, to a solution of 116.5 g (1 mole) of sodium monochloroacetate dissolved in 600 g of water, was added a solution of 310.8 g (1 mole) of 4-(2-hydroxy)dodecyl-7-methyl-3,6-dihydro-2H-1,4-diazepin-5-one dissolved in 150 g of dioxane. The acetate radical formation was effected at 50° to 60° C. to obtain 4-(2-hydroxy)dodecyl-7-methyl-1-azonia-4-azacyclohept-7-en-5-one-1-acetate.

Elementary analysis: $C_{20}H_{36}O_4N_2$; Calculated (%)—C 65.13, H 9.84, N 7.59, Found (%)—C 65.17, H 9.80, N 7.57.

IR spectrum—1635 cm⁻¹

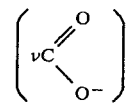

NMR spectrum—N+-CH₂COO⁻ proton 2.10 ppm (δ, DSS standard, 50 MHz).

EXAMPLE 27

Into an apparatus similar to that in Example 1, were charged 284.5 g (1 mole) of N-(2-hydroxy)tetradecylpropylenediamine and 130.1 g (1 mole) of ethyl acetoacetate. At 150° to 160° C., 18 g of water and 46 g of ethanol were distilled off to obtain white waxy 1-(2-hydroxy)tetradecyl-4-methyl-3,6,7,8-tetrahydro-1,5-diazocin-2-one.

Elementary analysis: $C_{21}H_{38}O_2N_2$; Calculated (%)—C 71.96, H 10.93, N 7.99, Found (%)—C 71.96, H 10.97, N 8.03.

Amine value—160.3 (theoretical 160.1).

IR spectrum—1615 cm⁻¹ ($v_{C=N}$), 1655 cm⁻¹ ($v_{C=O}$, amide).

Subsequently, to a solution of 116.5 g (1 mole) of sodium monochloroacetate dissolved in 600 g of water, was added a solution of 350.5 g (1 mole) of 1-(2-hydroxy)tetradecyl-4-methyl-3,6,7,8-tetrahydro-1,5-diazocin-2-one dissolved in 200 g of ethanol. The acetate radical formation was effected at 50° to 60° C. to obtain 1-(2-hydroxy)tetradecyl-4-methyl-1-aza-5-azoniacyclooct-4-en-2-one-5-acetate.

Elementary analysis: $C_{23}H_{40}O_4N_2$; Calculated (%)—C 67.62, H 9.87, N 6.85, Found (%)—C 67.60, H 9.91, N 6.89.

IR spectrum—1640 cm⁻¹

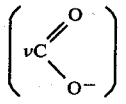

NMR spectrum—N+-CH₂COO⁻ proton 2.11 ppm (δ, DSS standard, 50 MHz).

EXAMPLE 28

Into an apparatus similar to that in Example 1, were charged 313.5 g (1 mole) of N-(2-hydroxy)tetradecyldiethylenetriamine and 158.1 g (1 mole) of butyl acetoacetate. At 150° to 160° C. and under a reduced pressure of 50 mmHg, 18 g of water and 74 g of butanol were distilled off to obtain 4-(2-hydroxytetradecyl)aminoethyl-7-methyl-3,6-dihydro-2H-1,4-diazepin-5-one.

Elementary analysis: $C_{22}H_{41}O_2N_3$; Calculated (%)—C 69.62, H 10.89, N 11.07, Found (%)—C 69.65, H 10.85, N 11.10.

Amine value—296.0 (theoretical 295.7).

IR spectrum—1610 cm⁻¹ ($v_{C=N}$), 1660 cm⁻¹ ($v_{C=O}$, amide).

Subsequently, to a solution of 94.5 g (1 mole) of monochloroacetic acid dissolved in 450 g of water, was added dropwise 379.5 g (1 mole) of the formed 4-(2-hydroxytetradecyl)aminoethyl-7-methyl-3,6-dihydro-2H-1,4-diazepin-5-one. After mixing at 60° to 70° C. and further addition of 40.0 g (1 mole) of sodium hydroxide, the reaction was allowed to proceed at the same temperature to obtain 4-(2-hydroxytetradecyl)aminoethyl-7-methyl-1-azonia-4-azacyclohept-7-en-5-one-1-acetate.

Elementary analysis: $C_{24}H_{43}O_4N_3$; Calculated (%)—C 65.88, H 9.91, N 9.60, Found (%)—C 65.86, H 9.90, N 9.58.

IR spectrum—1645 cm$^{-1}$

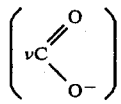

NMR spectrum—$N^+$-$CH_2COO^-$ proton 2.10 ppm ($\delta$, DSS standard, 50 MHz).

EXAMPLE 29

Into an apparatus similar to that in Example 1, were charged 339.5 g (1 mole) of N-(2-hydroxy)hexadecyldiethylenetriamine and 116.1 g (1 mole) of methyl acetoacetate. At 140° to 150° C., 18 g of water and 32 g of methanol were distilled off to obtain 4-(2-hydroxyhexadecyl)aminoethyl-7-methyl-3,6-dihydro-2H-1,4-diazepin-5-one.

Elementary analysis: $C_{24}H_{43}O_2N_3$; Calculated (%)—C 71.08, H 10.69, N 10.36, Found (%)—C 71.03, H 10.70, N 10.36.

Amine value—276.2 (theoretical 276.7).

IR spectrum—1610 cm$^{-1}$ ($\nu_{C=N}$), 1655 cm$^{-1}$ ($\nu_{C=O}$, amide).

Subsequently, to a solution of 405.5 g (1 mole) of 4-(2-hydroxyhexadecyl)aminoethyl-7-methyl-3,6-dihydro-2H-1,4-diazepin-5-one dissolved in 200 g of isopropyl alcohol, was added 132.6 g (1 mole) of potassium monochloroacetate dissolved in 600 g of water. The acetate radical formation was effected at 60° to 70° C. to obtain 4-(2-hydroxyhexadecyl)aminoethyl-7-methyl-1-azonia-4-azacyclohept-7-en-5-one-1-acetate.

Elementary analysis: $C_{26}H_{45}O_4N_3$; Calculated (%)—C 67.37, H 9.79, N 9.06, Found (%)—C 67.40, H 9.82, N 9.07.

IR spectrum—1645 cm$^{-1}$

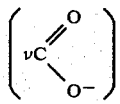

NMR spectrum—$N^+$-$CH_2COO^-$ proton 2.10 ppm ($\delta$, DSS standard, 50 MHz).

EXAMPLE 30

Into an apparatus similar to that in Example 1, were charged 484.8 g (1 mole) of a mono(2-hydroxy)docosyl derivative of a 1,3-propylenediamine-poly-(2 moles on the average)ethyleneimine adduct and 116.1 g (1 mole) of methyl acetoacetate. At 160° to 170° C., 18 g of water and 32 g of methanol were distilled off to obtain 1-(2-hydroxy)aminoethylaminoethyl-4-methyl-3,6,7,8-tetrahydro-1,5-diazocin-2-one.

Elementary analysis: $C_{33}H_{66}O_2N_4$; Calculated (%)—C 71.96, H 12.08, N 10.17, Found (%)—C 71.80, H 12.06, N 10.18.

Amine value—308.8 (theoretical 305.6).

IR spectrum—1615 cm$^{-1}$ ($\nu_{C=N}$), 1660 cm$^{-1}$ ($\nu_{C=O}$, amide).

Subsequently, to a solution of 161.0 g (1 mole) of sodium monochloroacetate dissolved in 900 g of water, was added dropwise 550.8 g (1 mole) of 1-(2-hydroxy)docosylaminoethylaminoethyl-4-methyl-3,6,7,8-tetrahydro-1,5-diazocin-2-one. The acetate radical formation was effected at 70° to 80° C. to obtain 1-(2-hydroxy)docosylaminoethylaminoethyl-4-methyl-1-aza-5-azoniacyclooct-4-en-2-one-5-acetate.

Elementary analysis: $C_{35}H_{68}O_4N_4$; Calculated (%)—C 69.04, H 11.26, N 9.20, Found (%)—C 69.00 H 11.30, N 9.19.

IR spectrum—1640 cm$^{-1}$

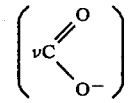

NMR spectrum—$N^+$-$CH_2COO^-$ proton 2.13 ppm ($\delta$, DSS standard, 50 MHz).

EXAMPLE 31

Into an apparatus similar to that in Example 1, were charged 218.3 g (1 mole) of N-octoxy(2-hydroxy)propylethylenediamine and 130.1 g (1 mole) of ethyl acetoacetate. At 150° to 160° C., 18 g of water and 46 g of ethanol were distilled off to obtain 4-octoxy(2-hydroxy)propyl-7-methyl-3,6-dihydro-2H-1,4-diazepin-5-one.

Elementary analysis: $C_{15}H_{28}O_3N_2$; Calculated (%)—C 63.36, H 9.93, N 9.85, Found (%)—C 63.35, H 9.92, N 9.88.

Amine value—197.3 (theoretical 197.3).

IR spectrum—1620 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 600 g of water, was added dropwise 284.3 g (1 mole) of 4-octoxy(2-hydroxy)propyl-7-methyl-3,6-dihydro-2H-1,4-diazepin-5-one. The acetate radical formation was effected at 50° to 60° C. to obtain 4-octoxy(2-hydroxy)propyl-7-methyl-1-azonia-4-azacyclohept-7-en-5-one-1-acetate.

Elementary analysis: $C_{17}H_{30}O_5N_2$; Calculated (%)—C 59.64, H 8.83, N 8.18, Found (%)—C 59.60, H 8.83, N 8.21.

IR spectrum—1650 cm$^{-1}$

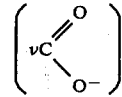

NMR spectrum—$N^+$-$CH_2COO^-$ proton 2.11 ppm ($\delta$, DSS standard, 50 MHz).

EXAMPLE 32

Into an apparatus similar to that in Example 1, were charged 465.7 g (1 mole) of N-nonylphenoxy(2-hydroxy)propyltetraethylenepentamine and 130.1 g (1 mole) of ethyl acetoacetate. At 150° to 160° C., 18 g of water and 46 g of ethanol were distilled off to obtain 4-nonylphenoxy(2-hydroxy)propylaminoethylaminoethyl-7-methyl-3,6-dihydro-2H-1,4-diazepin-5-one.

Elementary analysis: $C_{30}H_{53}O_3N_5$; Calculated (%)—C 67.77, H 10.05, N 13.17, Found (%)—C 67.80, H 10.06, N 13.16.

Amine value—424.0 (theoretical 422.1).

IR spectrum—1610 cm$^{-1}$ ($\nu_{C=N}$), 1655 cm$^{-1}$ ($\nu_{C=O}$, amide).

Subsequently, to a solution of 177.0 g (1 mole) of potassium monobromoacetate dissolved in 1,000 g of water, was added 531.7 g (1 mole) of 4-nonylphenoxy(2-hydroxy)propylaminoethylaminoethylaminoethyl-7-methyl-3,6-dihydro-2H-1,4-diazepin-5-one. The acetate radical formation was effected at 50° to 55° C. to obtain 4-nonylphenoxy(2-hydroxy)propylaminoethylaminoethylaminoethyl-7-methyl-1-azonia-4-azacyclohept-7-en-5-one-1-acetate.

Elementary analysis: $C_{32}H_{55}O_5N_5$; Calculated (%)—C 65.18, H 9.40, N 11.87, Found (%)—C 65.15, H 9.41, N 11.90.

IR spectrum—1655 cm$^{-1}$

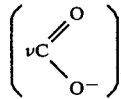

NMR spectrum—N$^+$-CH$_2$COO$^-$ proton 2.11 ppm (δ, DSS standard, 50 MHz).

EXAMPLE 33

Into an apparatus similar to that in Example 1, were charged 316.5 g (1 mole) of N-docoxy(2-hydroxy)propylpropylenediamine and 116.1 g (1 mole) of methyl acetoacetate. At 145° to 155° C., 18 g of water and 32 g of methanol were distilled off to obtain 1-docoxy(2-hydroxy)propyl-4-methyl-3,6,7,8-tetrahydro-1,5-diazocin-2-one.

Elementary analysis: $C_{22}H_{42}O_3N_2$; Calculated (%)—C 69.08, H 11.07, N 7.32, Found (%)—C 69.08, H 11.09, N 7.35.

Amine value—146.7 (theoretical 146.7).

IR spectrum—1617 cm$^{-1}$ ($\nu_{C=O}$), 1655 cm$^{-1}$ ($\nu_{C=O}$, amide).

Subsequently, to a solution of 107.6 g (1 mole) of monochloropropionic acid dissolved in 450 g of water, was added dropwise 382.5 g (1 mole) of 1-docoxy(2-hydroxy)propyl-4-methyl-3,6,7,8-tetrahydro-1,5-diazocin-2-one. After mixing at 50° to 60° C. and adding a solution of 56.1 g (1 mole) of potassium hydroxide dissolved in 200 g of water, the reaction was allowed to proceed at the same temperature to obtain 1-docoxy(2-hydroxy)propyl-4-methyl-1-aza-5-azoniacyclooct-4-en-2-one-5-propionate.

Elementary analysis: $C_{25}H_{46}O_5N_2$; Calculated (%)—C 66.06, H 10.20, N 6.16, Found (%)—C 66.10, H 10.18, N 6.18.

IR spectrum—1645 cm$^{-1}$

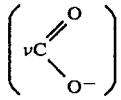

NMR spectrum—

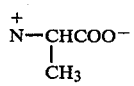

methyne proton 2.40 ppm (δ, DSS standard, 50 MHz).

EXAMPLE 34

Into an apparatus similar to that in Example 1, were charged 314.5 g (1 mole) of N-dodecyltriethylenetetramine and 116.1 g (1 mole) of methyl acetoacetate. At 140° to 150° C., 18 g of water and 32 g of methanol were distilled off to obtain 4-dodecylaminoethylaminoethyl-7-methyl-3,6-dihydro-2H-1,4-diazepin-5-one.

Elementary analysis: $C_{22}H_{44}ON_4$; Calculated (%)—C 69.42, H 11.65, N 14.71, Found (%)—C 69.48, H 11.68, N 14.72.

Amine value—444.2 (theoretical 442.2).

IR spectrum—1615 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 700 g of water, was added dropwise 380.6 g (1 mole) of 4-dodecylaminoethylaminoethyl-7-methyl-3,6-dihydro-2H-1,4-diazepin-5-one. The acetate radical formation was effected at 50° to 60° C. to synthesize 4-dodecylaminoethylaminoethyl-1-azonia-4-azacyclohept-7-en-5-one-1-acetate.

Elementary analysis: $C_{24}H_{46}O_3N_4$; Calculated (%)—C 65.72, H 10.57, N 12.77, Found (%)—C 65.75, H 10.55, N 12.79.

IR spectrum—1640 cm$^{-1}$

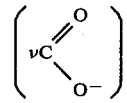

NMR spectrum—N$^+$-CH$_2$COO$^-$ proton 2.08 ppm (δ, DSS standard, 50 MHZ).

EXAMPLE 35

Into an apparatus similar to that in Example 1, were charged 299.5 g (1 mole) of N-tetradecyldiethylenetriamine and 116.1 g (1 mole) of methyl acetoacetate. At 150° to 160° C., 18 g of water and 32 g of methanol were distilled off to obtain 4-tetradecylaminoethyl-7-methyl-3,6-dihydro-2H-1,4-diazepin-5-one.

Elementary analysis: $C_{22}H_{43}ON_3$; Calculated (%)—C 72.27, H 11.86, N 11.49, Found (%)—C 72.26, H 11.88, N 11.52.

Amine value—306.8 (theoretical 306.9).

IR spectrum—1615 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 700 g of water, was added dropwise 365.6 g (1 mole) of 4-tetradecylaminoethyl-7-methyl-3,6-dihydro-2H-1,4-diazepin-5-one. The acetate radical formation was effected at 60° to 70° C. to obtain 4-tetradecylaminoethyl-7-methyl-1-azonia-4-azacyclohept-7-en-5-one-1-acetate.

Elementary analysis: $C_{24}H_{45}O_3N_3$; Calculated (%)—C 68.05, H 10.71, N 9.92; Found (%)—C 68.06, H 10.73, N 9.91.

IR spectrum—1635 cm$^{-1}$

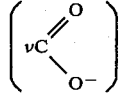

NMR spectrum—N$^+$-CH$_2$COO$^-$ proton 2.08 ppm (δ, DSS standard, 50 MHz).

EXAMPLE 36

Into an apparatus similar to that in Example 1, were charged 299.5 g (1 mole) of N-dodecyldipropylenetriamine and 130.1 g (1 mole) of ethyl acetoacetate. At 150° to 160° C., 18 g of water and 46 g of ethanol were distilled off to obtain 1-dodecylaminopropyl-4-methyl-3,6,7,8-tetrahydro-1,5-diazocin-2-one.

Elementary analysis: $C_{22}H_{43}ON_3$; Calculated (%)—C 72.29, H 11.86, N 11.49, Found (%)—C 72.33, H 11.88, N 11.46.

Amine value—308.1 (theoretical 307.0).

IR spectrum—1615 cm$^{-1}$ ($\nu_{C=N}$), 1655 cm$^{-1}$ ($\nu_{C=O}$, amide).

Subsequently, to a solution of 132.6 g (1 mole) of potassium monochloroacetate dissolved in 800 g of water, was added dropwise 365.5 g (1 mole) of 1-dodecylaminopropyl-4methyl-3,6,7,8-tetrahydro-1,5-diazocin-2-one. The acetate radical formation was effected at 60° to 70° C. to obtain 1-dodecylaminopropyl-4-methyl-1-aza-5-azoniacyclooct-4-en-2-one-5-acetate.

Elementary analysis: $C_{24}H_{45}O_3N_3$; Calculated (%)—C 68.06, H 10.71, N 9.92, Found (%)—C 68.09, H 10.72, N 9.95.

IR spectrum—1635 cm$^{-1}$

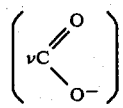

NMR spectrum—N$^+$-CH$_2$COO$^-$ proton 2.06 ppm (δ, DSS standard, 50 MHz).

EXAMPLE 37

Into an apparatus similar to that in Example 1, were charged 381.7 g (1 mole) of N-octadecyldipropylenetriamine and 130.1 g (1 mole) of ethyl acetoacetate. At 150° to 160° C., 18 g of water and 46 g of ethanol were distilled off to obtain 1-octadecylaminopropyl-4-methyl-3,6,7,8-tetrahydro-1,5-diazocin-2-one.

Elementary analysis: $C_{28}H_{53}ON_3$; Calculated (%)—C 75.11, H 11.93, N 9.38, Found (%)—C 75.14, H 11.93, N 9.40.

Amine value—250.9 (theoretical 250.6).

IR spectrum—1610 cm$^{-1}$ ($\nu_{C=N}$), 1660 cm$^{-1}$ ($\nu_{C=O}$, amide).

Subsequently, to a solution of 107.6 g (1 mole) of monochloropropionic acid dissolved in 600 g of water, was added dropwise 447.7 g (1 mole) of 1-octadecylaminopropyl-4-methyl-3,6,7,8-tetrahydro-1,5-diazocin-2-one. After mixing at 70° to 80° C. and adding 40.0 g (1 mole) of sodium hydroxide, the reaction was allowed to proceed at the same temperature to obtain 1-octadecylaminopropyl-4-methyl-1-aza-5-azoniacyclooct-4-en-2-one-5-propionate.

Elementary analysis: $C_{31}H_{57}O_3N_3$; Calculated (%)—C 71.63, H 11.05, N 8.08, Found (%)—C 71.60, H 11.08, N 8.09.

IR spectrum—1640 cm$^{-1}$

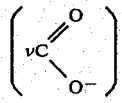

NMR spectrum—

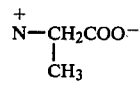

methyne proton 2.36 ppm (δ, DSS standard, 50 MHz).

EXAMPLE 38

Into an apparatus similar to that in Example 1, were charged 385.6 g (1 mole) of a monododecyl-derivative of an adduct of dipropylenetriamine with 2 moles of ethyleneimine and 158.1 g of butyl acetoacetate. At 155° to 160° C. and under a reduced pressure of 40 mmHg, 18 g of water and 74 g of butanol were distilled off to obtain 1-dodecylaminoethylaminoethylaminopropyl-4-methyl-3,6,7,8-tetrahydro-1,5-diazocin-2-one.

Elementary analysis: $C_{26}H_{53}ON_5$; Calculated (%)—C 69.15, H 11.83, N 15.50, Found (%)—C 69.20, H 11.87, N 15.53.

Amine value—500.0 (theoretical 496.9).

IR spectrum—1610 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 800 g of water, was added dropwise 451.6 g (1 mole) of 1-dodecylaminoethylaminoethylaminopropyl-4-methyl-3,6,7,8-tetrahydro-1,5-diazocin-2-one. The acetate radical formation was effected at 60° to 70° C. to obtain 1-dodecylaminoethylaminoethylaminopropyl-4-methyl-1-aza-5-azoniacyclooct-4-en-2-one-5-acetate.

Elementary analysis: $C_{28}H_{55}O_3N_5$; Calculated (%)—C 65.99, H 10.88, N 13.74, Found (%)—C 66.03, H 10.85, N 13.80.

IR spectrum—1640 cm$^{-1}$

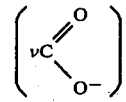

NMR spectrum—N$^+$-CH$_2$COO$^-$ proton 2.10 ppm (δ, DSS standard, 50 MHz).

EXAMPLE 39

Into an apparatus similar to that in Example 1, were charged 338.5 g (1 mole) of N-methylbenzylpoly(2 moles)oxypropyleneoxypropylethylenediamine and 116.1 g (1 mole) of methyl acetoacetate. At 140° to 150° C., 18 g of water and 32 g of methanol were distilled off to obtain 4-methylbenzylpoly(2moles)oxypropyleneoxypropyl-7-methyl-3,6-dihydro-2H-1,4-diazepin-5-one.

Elementary analysis: $C_{23}H_{36}O_4N_2$; Calculated (%)—C 68.29, H 8.97, N 6.92, Found (%)—C 68.32, H 8.95, N 6.93.

Amine value—139.5 (theoretical 138.7).

IR spectrum—1615 cm$^{-1}$ ($\nu_{C=N}$), 1655 cm$^{-1}$ ($\nu_{C=O}$, amide).

Subsequently, to a solution of 116.5 g (1 mole) of sodium chloroacetate dissolved in 600 g of water, was added dropwise 404.5 g (1 mole) of 4-methylbenzylpoly(2moles)oxypropyleneoxypropyl-7-methyl-3,6-dihydro-2H-1,4-diazepin-5-one. The acetate radical formation was effected at 50° to 60° C. to obtain 4-methylbenzylpoly(2 moles)oxypropyleneoxypropyl-7-methyl-1-azonia-4-azacyclohept-7-en-5-one-1-acetate.

Elementary analysis: $C_{25}H_{38}O_6N_2$; Calculated (%)—C 64.92, H 8.28, N 6.05, Found (%)—C 64.96, H 8.26, N 6.06.

IR spectrum—1640 cm$^{-1}$

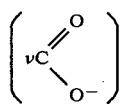

NMR spectrum—$N^+$-$CH_2COO^-$ proton 2.10 ppm ($\delta$, DSS standard, 50 MHz).

EXAMPLE 40

Into an apparatus similar to that in Example 1, were charged 299.5 g (1 mole) of N-tetradecyldiethylenetriamine and 116.1 g (1 mole) of methyl 2-formylpropionate. At 130° to 135° C., 18 g of water and 32 g of methanol were distilled off to obtain 4-tetradecylaminoethyl-6-methyl-3,6-dihydro-2H-1,4-diazepin-5-one.

Elementary analysis: $C_{22}H_{43}ON_3$; Calculated (%)—C 72.27, H 11.86, N 11.49, Found (%)—C 72.30, H 11.88, N 11.46.

Amine value—306.8 (theoretical 306.9).

IR spectrum—1618 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 600 g of water, was added dropwise 365.6 g (1 mole) of 4-tetradecylaminoethyl-6-methyl-3,6-dihydro-2H-1,4-diazepin-5-one. The acetate radical formation was effected at 50° to 60° C. to obtain 4-tetradecylaminoethyl-6-methyl-1-azonia-4-azacyclohept-7-en-5-one-1-acetate.

Elementary analysis: $C_{24}H_{45}O_3N_3$; Calculated (%)—C 68.05, H 10.71, N 9.92, Found (%)—C 68.03, H 10.73, N 9.94.

IR spectrum—1635 cm$^{-1}$

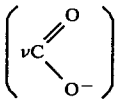

NMR spectrum—$N^+$-$CH_2COO^-$ proton 2.08 ppm ($\delta$, DSS standard, 50 MHz).

EXAMPLE 41

Into an apparatus similar to that in Example 1, were charged 339.5 g (1 mole) of N-(2-hydroxy)hexadecyldiethylenetriamine and 130.1 g of ethyl 2-formylpropionate. At 140° to 150° C., 18 g of water and 46 g of ethanol were distilled off to obtain 4-(2-hydroxyhexadecyl)aminoethyl-6-methyl-3,6-dihydro-2H-1,4-diazepin-5-one.

Elementary analysis: $C_{24}H_{43}O_2N_3$; Calculated (%)—C 71.08, H 10.69, N 10.36, Found (%)—C 71.10, H 10.71, N 10.36.

Amine value—276.5 (theoretical 276.7).

IR spectrum—1615 cm$^{-1}$ ($\nu_{C=N}$), 1655 cm$^{-1}$ ($\nu_{C=O}$, amide).

Subsequently, to a solution of 405.5 g (1 mole) of 4-(2-hydroxyhexadecyl)aminoethyl-6-methyl-3,6-dihydro-2H-1,4-diazepin-5-one dissolved in 200 g of dioxane, was added a solution of 132.6 g (1 mole) of potassium monochloroacetate dissolved in 600 g of water. The acetate radical formation was effected at 60° to 70° C. to obtain 4-(2-hydroxyhexadecyl)aminoethyl-6-methyl-1-azonia-4-azacyclohept-7-en-5-one-1-acetate.

Elementary analysis: $C_{26}H_{45}O_4N_3$; Calculated (%)—C 67.37, H 9.79, N 9.06, Found (%)—C 67.41, H 9.78, N 9.06.

IR spectrum—1645 cm$^{-1}$

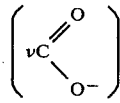

NMR spectrum—$N^+$-$CH_2COO^-$ proton 2.09 ppm ($\delta$, DSS standard, 50 MHz).

EXAMPLE 42

Into an apparatus similar to that in Example 1, were charged 228.1 g (1 mole) of N-dodecylethylenediamine and 130.1 g (1 mole) of ethyl 2-formylpropionate. At 140° to 145° C., 18 g of water and 46 g of ethanol were distilled off to obtain 4-dodecyl-6-methyl-3,6-dihydro-2H-1,4-diazepin-5-one.

Elementary analysis: $C_{18}H_{34}ON_2$; Calculated (%)—C 73.48, H 11.64, N 9.52, Found (%)—C 73.51, H 11.68, N 9.54.

Amine value—192.1 (theoretical 190.8).

IR spectrum—1610 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 600 g of water, was added dropwise 294.2 g (1 mole) of 4-dodecyl-6-methyl-3,6-dihydro-2H-1,4-diazepin-5-one. The acetate radical formation was effected at 50° to 60° C. to obtain 4-dodecyl-6-methyl-1-azonia-4-azacyclohept-7-en-5-one-1-acetate.

Elementary analysis: $C_{20}H_{36}O_3N_2$; Calculated (%)—C 68.20, H 10.30, N 7.95, Found (%)—C 68.25, H 10.31, N 7.98.

IR spectrum—1640 cm$^{-1}$

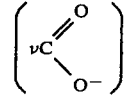

NMR spectrum—$N^+$-$CH_2COO^-$ proton 2.05 ppm ($\delta$, DSS standard, 50 MHz).

EXAMPLE 43

Into an apparatus similar to that in Example 1, were charged 244.8 g (1 mole) of N-(2-hydroxy)dodecylethylenediamine and 144.2 g (1 mole) of isopropyl 2-formylpropionate. At 150° to 155° C., 18 g of water and 60 g of isopropyl alcohol were distilled off to obtain 4-(2-hydroxy)dodecyl-6-methyl-3,6-dihydro-2H-1,4-diazepin-5-one.

Elementary analysis: $C_{18}H_{34}O_2N_2$; Calculated (%)—C 69.56, H 11.03, N 9.01, Found (%)—C 69.39, H 11.05, N 9.05.

Amine value—180.5 (theoretical 180.5).

IR spectrum—1620 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 600 g of water, was added a solution of 310.8 g (1 mole) of 4-(2-hydroxy)dodecyl-6-methyl-3,6-dihydro-2H-1,4-diazepin-5-one dissolved in 150 g of ethanol. The acetate radical formation was effected at 50° to 60° C. to obtain 4-(2-hydroxy)dodecyl-6-methyl-1-azonia-4-azacyclohept-7-en-5-one-1-acetate.

Elementary analysis: $C_{20}H_{36}O_4N_2$; Calculated (%)—C 65.13, H 9.84, N 7.59, Found (%)—C 65.15, H 9.80, N 7.60.

IR spectrum—1635 cm$^{-1}$

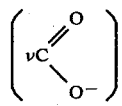

NMR spectrum—$N^+$-$CH_2COO^-$ proton 2.08 ppm ($\delta$, DSS standard, 50 MHz).

EXAMPLE 44

Into an apparatus similar to that in Example 1, were charged 242.1 g (1 mole) of N-dodecylpropylenediamine and 130.1 g (1 mole) of ethyl 2-formylpropionate. At 145° to 150° C., 18 g of water and 46 g of ethanol were distilled off to obtain 1-dodecyl-3,6,7,8-tetrahydro-1,5-diazocin-2-one.

Elementary analysis: $C_{19}H_{36}ON_2$; Calculated (%)—C 74.04, H 11.77, N 9.09, Found (%)—C 74.03, H 11.76, N 9.09.

Amine value—181.9 (theoretical 182.1).

IR spectrum—1610 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 600 g of water, was added dropwise 308.2 g (1 mole) of 1-dodecyl-3-methyl-3,6,7,8-tetrahydro-1,5-diazocin-2-one. The acetate radical formation was effected at 60° to 70° C. to obtain 1-dodecyl-3-methyl-1-aza-5-azoniacyclooct-4-en-2-one-5-acetate.

Elementary analysis: $C_{21}H_{38}O_3N_2$; Calculated (%)—C 68.67, H 10.46, N 7.65, Found (%)—C 68.68, H 10.49, N 7.65.

IR spectrum—1635 cm$^{-1}$

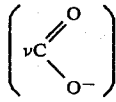

NMR spectrum—$N^+$-$CH_2$-$COO^-$ proton 2.09 ppm ($\delta$, DSS standard, 50 MHz).

EXAMPLE 45

Into an apparatus similar to that in Example 1, were charged 256.5 g (1 mole) of N-(2-hydroxy)dodecylpropylenediamine and 116.1 g (1 mole) of methyl 2-formylpropionate. At 130° to 135° C., 18 g of water and 32 g of methanol were distilled off to obtain 1-(2-hydroxy)-dodecyl-3-methyl-3,6,7,8-tetrahydro-1,5-diazocin-2-one.

Elementary analysis: $C_{19}H_{34}O_2N_2$; Calculated (%)—C 75.97, H 10.63, N 8.68, Found (%)—C 76.00, H 10.62, N 8.71.

Amine value—174.1 (theoretical 173.9).

IR spectrum—1615 cm$^{-1}$ ($\nu_{C=N}$), 1655 cm$^{-1}$ ($\nu_{C=O}$, amide).

Subsequently, into a solution of 116.5 g (1 mole) of sodium monochloroacetate dissolved in 600 g of water, was added dropwise 322.5 g (1 mole) of 1-(2-hydroxy)-dodecyl-3-methyl-3,6,7,8-tetrahydro-1,5-diazocin-2-one. The acetate radical formation was effected at 50° to 60° C. to obtain 1-(2-hydroxy)dodecyl-3-methyl-1-aza-5-azoniacyclooct-4-en-2-one-5-acetate.

Elementary analysis: $C_{21}H_{36}O_4N_2$; Calculated (%)—C 66.28, H 9.54, N 7.36, Found (%)—C 66.30, H 9.50, N 7.38.

IR spectrum—1635 cm$^{-1}$

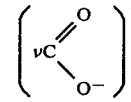

NMR spectrum—$N^+$-$CH_2COO^-$ proton 2.08 ppm ($\delta$, DSS standard, 50 MHz).

EXAMPLE 46

Into an apparatus similar to that in Example 1, were charged 103.1 g (1 mole) of diethylenetriamine and 116.1 g (1 mole) of methyl 2-formylpropionate. At 130° to 135° C., 18 g of water and 32 g of methanol were distilled off. Then, after addition of 200.3 g (1 mole) of lauric acid, the amide formation was effected at 200° to 210° C. to distil off 18 g of water, leaving behind 4-lauramidoethyl-6-methyl-3,6-dihydro-2H-1,4-diazepin-5-one.

Elementary analysis: $C_{20}H_{37}O_2N_3$; Calculated (%)—C 68.37, H 10.62, N 11.96, Found (%)—C 68.38, H 10.62, N 11.99.

Amine value—161.2 (theoretical 159.7).

IR spectrum—1610 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 400 g of water, was added dropwise a solution of 351.3 g (1 mole) of 4-lauramidoethyl-6-methyl-3,6-dihydro-2H-1,4-diazepin-5-one dissolved in 400 g of methanol. The acetate radical formation was effected at 55° to 60° C. to obtain 4-lauramidoethyl-6-methyl-1-azonia-4-azacyclohept-7-en-5-one-1-acetate.

Elementary analysis: $C_{22}H_{39}O_4N_3$; Calculated (%)—C 64.55, H 9.60, N 10.26, Found (%)—C 64.58, H 9.61, N 10.23.

IR spectrum—1640 cm$^{-1}$

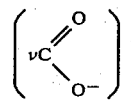

NMR spectrum—$N^+$-$CH_2COO^-$ proton 2.06 ppm ($\delta$, DSS standard, 50 MHz).

EXAMPLE 47

Into an apparatus similar to that in Example 1, were charged 104.2 g (1 mole) of N-hydroxyethylenediamine and 130.1 g (1 mole) of ethyl 2-formylpropionate. At 145° to 150° C., 18 g of water and 46 g of ethanol were distilled off. Then, after addition of 200.3 g (1 mole) of lauric acid, esterification was carried out while distilling off 18 g of water to obtain 4-lauroyloxyethyl-6-methyl-3,6-dihydro-2H-1,4-diazepin-5-one.

Elementary analysis: $C_{20}H_{36}O_3N_2$; Calculated (%)—C 68.12, H 10.29, N 7.94, Found (%)—C 68.15, H 10.28, N 7.96.

Amine value—159.5 (theoretical 159.1).

IR spectrum—1610 cm$^{-1}$ ($\nu_{C=N}$), 1650 cm$^{-1}$ ($\nu_{C=O}$, amide), 1740 cm$^{-1}$ ($\nu_{C=O}$, ester).

Subsequently, to 116.5 g (1 mole) of sodium monochloroacetate dissolved in 800 g of water, was added dropwise 352.6 g (1 mole) of 4-lauroyloxyethyl-6-methyl-3,6-dihydro-2H-1,4-diazepin-5-one. The acetate radical formation was carried out at 60° to 70° C. to obtain 4-lauroyloxyethyl-6-methyl-1-azonia-4-azacyclohept-7-en-5-one-1-acetate.

Elementary analysis: $C_{22}H_{38}O_5N_2$; Calculated (%)—C 64.35, H 9.33, N 6.82, Found (%)—C 64.36, H 9.36, N 6.78.

IR spectrum—1635 cm$^{-1}$

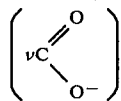

NMR spectrum—N$^+$-CH$_2$COO$^-$ proton 2.08 ppm (δ, DSS standard, 50 MHz).

EXAMPLE 48

Into an apparatus similar to that in Example 1, were charged 313.5 g (1 mole) of N-monotetradecylaminoethylpropylenediamine and 116.1 g (1 mole) of methyl-2-formylpropionate. At 130° to 135° C., 18 g of water and 32 g of methanol were distilled off to obtain 1-tetradecylaminoethyl-3-methyl-3,6,7,8-tetrahydro-1,5-diazocin-2-one.

Elementary analysis: $C_{23}H_{45}ON_3$; Calculated (%)—C 72.76, H 11.96, N 11.06, Found (%)—C 72.77, H 11.99, N 11.08.

Amine value—295.4 (theoretical 295.6).

IR spectrum—1615 cm$^{-1}$ ($\nu_{C=N}$), 1660 cm$^{-1}$ ($\nu_{C=O}$, amide).

Subsequently, to a solution of 107.6 g (1 mole) of monochloropropionic acid dissolved in 600 g of water, was added dropwise 379.6 g (1 mole) of 1-tetradecylaminoethyl-3-methyl-3,6,7,8-tetrahydro-1,5-diazocin-2-one. After mixing at 70° to 80° C. and addition of 40.0 g (1 mole) of sodium hydroxide, the reaction was allowed to proceed at the same temperature to obtain 1-tetradecylaminoethyl-3-methyl-1-aza-5-azoniaclooct-4-en-2-one-5-propionate.

Elementary analysis: $C_{26}H_{49}O_3N_3$; Calculated (%)—C 69.14, H 10.94, N 9.30, Found (%)—C 69.15, H 10.95, N 9.32.

IR spectrum—1645 cm$^{-1}$

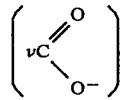

NMR spectrum—

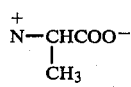

methyne proton 2.40 ppm (δ, DSS standard, 50 MHz).

EXAMPLE 49

Into an apparatus similar to that in Example 1, were charged 353.5 g (1 mole) of N-mono(2-hydroxy)hexadecylaminoethylpropylenediamine and 158.2 g (1 mole) of butyl 2-formyl propionate. At 155° C. and under a reduced pressure of 50 mmHg, 18 g of water and 74 g of butanol were distilled off to obtain 1-(2-hydroxyhexadecyl)aminoethyl-3-methyl-3,6,7,8-tetrahydro-1,5-diazocin-2-one.

Elementary analysis: $C_{25}H_{45}O_2N_3$; Calculated (%)—C 71.55, H 10.82, N 10.01, Found (%)—C 71.59, H 10.81, N 10.00.

Amine value—268.0 (theoretical 267.3)

IR spectrum—1615 cm$^{-1}$ ($\nu_{C=N}$), 1655 cm$^{-1}$ ($\nu_{C=O}$, amide).

Subsequently, to a solution of 419.7 g (1 mole) of 1-(2-hydroxyhexadecyl)aminoethyl-3-methyl-3,6,7,8-tetrahydro-1,5-diazocin-2-one dissolved in 250 g of isopropyl alcohol, was added a solution of 132.6 g (1 mole) of potassium monochloroacetate dissolved in 600 g of water. The acetate radical formation was effected at 60° to 70° C. to obtain 1-(2-hydroxyhexadecyl)aminoethyl-3-methyl-1-aza-5-azoniacyclooct-4-en-2-one-5-acetate.

Elementary analysis: $C_{27}H_{47}O_4N_3$; Calculated (%)—C 67.89, H 9.92, N 8.79, Found (%)—C 67.92, H 9.89, N 8.81.

IR spectrum—1645 cm$^{-1}$

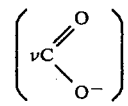

NMR spectrum—N$^+$-CH$_2$COO$^-$ proton 2.10 ppm (δ, DSS standard, 50 MHz).

EXAMPLE 50

Into an apparatus similar to that in Example 1, were charged 301.5 g (1 mole) of a monooctyl derivative of a 1,3-propylenediamine-poly(3moles on the average)ethyleneimine adduct and 130.1 g (1 mole) of ethyl 2-formylpropionate. At 130° to 140° C. and under a reduced pressure of 50 mmHg, 18 g of water and 46 g of ethanol were distilled off to synthesize N-alkylalkenelactam.

Elementary analysis: $C_{21}H_{42}ON_5$; Calculated (%)—C 66.23, H 11.12, N 18.38, Found (%)—C 66.28, H 11.14, N 18.33.

Amine value—590.1 (theoretical 589.4).

IR spectrum—1610 cm$^{-1}$ ($\nu_{C=N}$), 1655 cm$^{-1}$ ($\nu_{C=O}$, amide).

Subsequently, to a solution of 94.5 g (1 mole) of monochloroacetic acid dissolved in 500 g of water, was added dropwise 380.8 g (1 mole) of the formed N-alkylalkenelactam. After mixing at 60° to 70° C. and addition of 56.1 g (1 mole) of potassium hydroxide, the reaction was allowed to proceed at the same temperature to obtain the compound having an acetate radical.

Elementary analysis: $C_{23}H_{44}O_3N_5$; Calculated (%)—C 62.95, H 10.11, N 15.95, Found (%)—C 62.99, H 10.98, N 15.95.

IR spectrum—1640 cm$^{-1}$

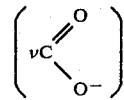

NMR spectrum—N$^+$-CH$_2$COO$^-$ proton 2.05 ppm (δ, DSS standard, 50 MHz).

EXAMPLE 51

Into an apparatus similar to that in Example 1, were charged 132.2 g (1 mole) of N-hydroxypropyl-1,3-propylenediamine and 116.1 g (1 mole) of methyl 2-formylpropionate. At 130° to 135° C., 18 g of water and 32 g of methanol were distilled off. Then, after adding 340.5 g (1 mole) of behenic acid, esterification was carried out at 180° to 190° C. under a reduced pressure of 70 mmHg, while distilling off 18 g of water, to obtain 1-behenoyloxypropyl-3-methyl-3,6,7,8-tetrahydro-1,5-diazocin-2-one.

Elementary analysis: $C_{32}H_{58}O_3N_2$; Calculated (%)—C 74.08, H 11.27, N 53.98, Found (%)—C 74.10, H 11.27, N 53.98.

Amine value—108.3 (theoretical 108.1).

IR spectrum—1615 cm$^{-1}$ ($\nu_{C=N}$), 1660 cm$^{-1}$ ($\nu_{C=O}$, amide), 1735 cm$^{-1}$ ($\nu_{C=O}$, ester).

Subsequently, to a solution of 518.8 g (1 mole) of 1-behenoyloxypropyl-3-methyl-3,6,7,8-tetrahydro-1,5-diazocin-2-one dissolved in 600 g of isopropyl alcohol, was added dropwise a solution of 177.0 g (1 mole) of potassium monobromoacetate dissolved in 600 g of water. The acetate radical formation was effected at 70° to 80° C. to obtain 1-behenoyloxypropyl-3-methyl-1-aza-5-azoniacyclooct-4-en-2-one-5-acetate.

Elementary analysis: $C_{34}H_{60}O_5N_2$; Calculated (%)—C 70.79, H 10.49, N 4.85, Found (%)—C 70.82, H 10.51, N 4.85.

IR spectrum—1640 cm$^{-1}$

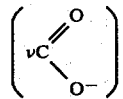

NMR spectrum—N$^+$-CH$_2$COO$^-$ proton 2.05 ppm ($\delta$, DSS standard, 50 MHz).

EXAMPLE 52

Into an apparatus similar to that in Example 1, were charged 465.7 g (1 mole) of N-nonylphenoxy(2-hydroxy)propyltetraethylenepentamine and 130.1 g (1 mole) of ethyl 2-formylpropionate. At 140° to 145° C., 18 g of water and 46 g of ethanol were distilled off to obtain 4-nonylphenoxy(2-hydroxy)propylaminoethylaminoethylaminoethyl-6-methyl-3,6-dihydro-2H-1,4-diazepin-5-one.

Elementary analysis: $C_{30}H_{53}O_3N_5$; Calculated (%)—C 67.77, H 10.05, N 13.17, Found (%)—C 67.81, H 10.05, N 13.19.

Amine value—423.5 (theoretical 422.1).

IR spectrum—1610 cm$^{-1}$ ($\nu_{C=O}$), 1660 cm$^{-1}$ ($\nu_{C=O}$, amide).

Subsequently, to a solution of 177.0 g (1 mole) of potassium monobromoacetate dissolved in 1,000 g of water, was added 531.7 g (1 mole) of 4-nonylphenoxy(2-hydroxy)propylaminoethylaminoethylaminoethyl-6-methyl-3,6-dihydro-2H-1,4-diazepin-5-one. The acetate radical formation was effected at 60° to 70° C. to obtain 4-nonylphenoxy(2-hydroxy)propylaminoethylaminoethylaminoethyl-6-methyl-1-azonia-4-azacyclohept-7-en-5-one-1-acetate.

Elementary analysis: $C_{32}H_{55}O_5N_5$; Calculated (%)—C 65.18, H 9.40, N 11.87, Found (%)—C 65.18, H 9.39, N 11.88.

IR spectrum—1650 cm$^{-1}$

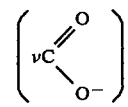

NMR spectrum—N$^+$-CH$_2$COO$^-$ proton 2.10 ppm ($\delta$, DSS standard, 50 MHz).

EXAMPLE 53

Into an apparatus similar to that in Example 1, were charged 299.5 g (1 mole) of N-tetradodecyldiethylenetriamine and 116.1 g (1 mole) of methyl 3-formylpropionate. At 125° to 130° C., 18 g of water and 32 g of methanol were distilled off to obtain 4-tetradecylaminoethyl-2,3,6,7-tetrahydro-1,4-diazocin-5-one.

Elementary analysis: $C_{22}H_{43}ON_3$; Calculated (%)—C 72.27, H 11.86, N 11.49, Found (%)—C 72.31, H 11.87, N 11.48.

Amine value—306.8 (theoretical 306.9)

IR spectrum—1615 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 700 g of water, was added dropwise 365.6 g (1 mole) of 4-tetradecylaminoethyl-2,3,6,7-tetrahydro-1,4-diazocin-5-one. The acetate radical formation was effected at 60° to 65° C. to obtain 4-tetradecylaminoethyl-4-aza-1-azoniacyclooct-8-en-5-one-1-acetate.

Elementary analysis: $C_{24}H_{45}O_3N_3$; Calculated (%)—C 68.05, H 10.71, N 9.92, Found (%)—C 68.09, H 10.74, N 9.90.

IR spectrum—1635 cm$^{-1}$

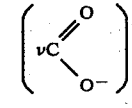

NMR spectrum—N$^+$-CH$_2$COO$^-$ proton 2.10 ppm ($\delta$, DSS standard, 50 MHz).

EXAMPLE 54

Into an apparatus similar to that in Example 1, were charged 339.5 g (1 mole) of N-(2-hydroxy)hexadecyldiethylenetriamine and 130.1 g (1 mole) of ethyl 3-formylpropionate. At 135° to 140° C., 18 g of water and 46 g of ethanol were distilled off to obtain 4-(2-hydroxyhexadecyl)aminoethyl-2,3,6,7-tetrahydro-1,4-diazocin-5-one.

Elementary analysis: $C_{24}H_{43}O_2N_3$; Calculated (%)—C 71.08, H 10.69, N 10.36, Found (%)—C 71.11, H 10.70, N 10.34.

Amine Value: 276.6 (theoretical 276.7).

IR spectrum: 1618 cm$^{-1}$ ($\nu_{C=N}$), 1655 cm$^{-1}$ ($\nu_{C=O}$, amide).

Subsequently, to a solution of 405.5 g (1 mole) of 4-(2-hydroxyhexadecyl)aminoethyl-2,3,6,7-tetrahydro-1,4-diazocin-5-one dissolved in 300 g of isopropyl alcohol, was added a solution of 132.6 g (1 mole) of potassium monochloroacetate dissolved in 600 g of water. The acetate radical formation was effected at 50° to 60° C. to obtain 4-(2-hydroxyhexadecyl)aminoethyl-4-aza-1-azoniacyclooct-8-en-5-one-1-acetate.

Elementary analysis: $C_{26}H_{45}O_4N_3$; Calculated (%)—C 67.37, H 9.79, N 9.06, Found (%)—C 67.36, H 9.78, N 9.06.

IR spectrum—1640 cm$^{-1}$

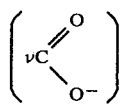

NMR spectrum—N$^+$-CH$_2$COO$^-$ proton 2.08 ppm (δ, DSS standard, 50 MHz).

EXAMPLE 55

Into an apparatus similar to that in Example 1, were charged 310.1 g (1 mole) of N-(9-octadecenyl)ethylenediamine and 158.2 g (1 mole) of butyl 3-formylpropionate. At 150° C. and under a reduced pressure of 50 mmHg, 18 g of water and 74 g of butanol were distilled off to obtain 4-(9-octadecenyl)-2,3,6,7-tetrahydro-1,4-diazocin-5-one.

Elementary analysis: $C_{24}H_{44}ON_2$; Calculated (%)—C 76.53, H 11.79, N 7.43, Found (%)—C 76.55, H 11.80, N 7.45.

Amine value—149.0 (theoretical 149.0).

IR spectrum—1610 cm$^{-1}$ ($\nu_{C=N}$), 1650 cm$^{-1}$ ($\nu_{C=O}$, amide).

Subsequently, to a solution of 94.5 g (1 mole) of monochloroacetic acid dissolved in 500 g of water, was added dropwise 376.6 g (1 mole) of the formed 4-(9-octadecenyl)-2,3,6,7-tetrahydro-1,4-diazocin-5-one. After mixing at 65° to 75° C. and further addition of 56.1 g (1 mole) of potassium hydroxide, the reaction was allowed to proceed at the same temperature to obtain 4-(9-octadecenyl)-4-aza-1-azoniacyclooct-8-en-5-one-1-acetate.

Elementary analysis: $C_{26}H_{46}O_3N_2$; Calculated (%)—C 71.84, H 10.67, N 6.44, Found (%)—C 71.80, H 10.65, N 6.46.

IR spectrum—1635 cm$^{-1}$

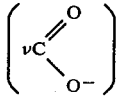

NMR spectrum—N$^+$-CH$_2$COO$^-$ proton 2.10 ppm (δ, DSS standard, 50 MHz).

EXAMPLE 56

Into an apparatus similar to that in Example 1, were charged 103.1 g (1 mole) of diethylenetriamine and 144.2 g (1 mole) of propyl 3-formylpropionate. At 140° to 145° C., 18 g of water and 60 g of propyl alcohol were distilled off. Then, after adding 144.2 g (1 mole) of octylic acid, the reaction was allowed to proceed at 150° to 155° C. to distil off 18 g of water, obtaining 4-octamidoethyl-2,3,6,7-tetrahydro-1,4-diazocin-5-one.

Elementary analysis: $C_{16}H_{29}O_2N_3$; Calculated (%)—C 65.09, H 9.90, N 14.23, Found (%)—C 65.08, H 9.89, N 14.24.

Amine value—192.2 (theoretical 190.1).

IR spectrum—1615 cm$^{-1}$ ($\nu_{C=N}$), 1655 cm$^{-1}$ ($\nu_{C=O}$, amide).

Subsequently, to a solution of 107.6 g (1 mole) of monochloropropionic acid dissolved in 600 g of water, was added dropwise 295.2 g (1 mole) of 4-octamidoethyl-2,3,6,7-tetrahydro-1,4-diazocin-5-one. After mixing at 70° to 80° C. and adding 40.0 g (1 mole) of sodium hydroxide, the reaction was allowed to proceed at the same temperature to obtain 4-octamidoethyl-4-aza-1-azoniacyclooct-8-en-5-one-1-propionate.

Elementary analysis: $C_{19}H_{33}O_4N_3$; Calculated (%)—C 62.09, H 9.06, N 11.43, Found (%)—C 62.05, H 9.04, N 11.43.

IR spectrum—1635 cm$^{-1}$

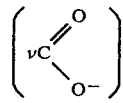

NMR spectrum—

$$\underset{CH_3}{\overset{+}{N}-CHCOO^-}$$

methyne proton 2.25 ppm (δ, DSS standard, 50 MHz).

EXAMPLE 57

Into an apparatus similar to that in Example 1, were charged 104.2 g (1 mole) of N-hydroxyethylethylenediamine and 116.1 g (1 mole) of methyl 3-formylpropionate. At 130° C., 18 g of water and 32 g of methanol were distilled off. After adding 340.5 g (1 mole) of behenic acid, esterification was carried out at 210° to 220°.C. to obtain 4-behenoyloxyethyl-2,3,6,7-tetrahydro-1,4-diazocin-5-one.

Elementary analysis: $C_{30}H_{54}O_3N_2$; Calculated (%)—C 73.43, H 11.09, N 5.71, Found (%)—C 73.41, H 11.09, N 5.74.

Amine value—115.0 (theoretical 114.3).

IR spectrum—1615 cm$^{-1}$ ($\nu_{C=N}$), 1660 cm$^{-1}$ ($\nu_{C=O}$, amide), 1735 cm$^{-1}$ ($\nu_{C=O}$, ester).

Subsequently, 490.7 g (1 mole) of 4-behenoyloxyethyl-2,3,6,7-tetrahydro-1,4-diazocin-5-one and 116.5 g (1 mole) of sodium monochloroacetate were allowed to react in the presence of 600 g of water and 600 g of ethanol to obtain 4-behenoyloxyethyl-4-aza-1-azoniacyclooct-8-en-5-one-1-acetate.

Elementary analysis: $C_{32}H_{56}O_5N_2$; Calculated (%)—C 70.04, H 10.28, N 5.10, Found (%)—C 70.08, H 10.31, N 5.08.

IR spectrum—1635 cm$^{-1}$

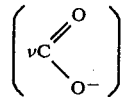

NMR spectrum—N$^+$-CH$_2$COO$^-$ proton 2.13 ppm (δ, DSS standard, 50 MHz).

EXAMPLE 58

Into an apparatus similar to that in Example 1, were charged 299.5 g (1 mole) of N-tetradecyldiethylenetriamine and 130.1 g (1 mole) of methyl 2-formyl-2-methylpropionate. At 140° to 145° C., 18 g of water and 32 g of methanol were distilled off to obtain 4-tetradecylaminoethyl-6,6-dimethyl-3-hydro-2H-1,4-diazepin-5-one.

Elementary analysis: $C_{23}H_{45}ON_3$; Calculated (%)—C 72.76, H 11.96, N 11.06, Found (%)—C 72.74, H 11.98, N 11.06.

Amine value—296.0 (theoretical 295.6).

IR spectrum—1615 cm$^{-1}$ ($\nu_{C=N}$), 1660 cm$^{-1}$ ($\nu_{C=O}$, amide).

Subsequently, to a solution of 107.6 g (1 mole) of monochloropropionic acid dissolved in 600 g of water, was added dropwise 379.6 g (1 mole) of 4-tetradecylaminoethyl-6,6-dimethyl-3-hydro-2H-1,4-diazepin-5-one. After mixing at 70° to 75° C. and adding 40.0 g (1 mole) of sodium hydroxide, the reaction was allowed to proceed at the same temperature to obtain 4-tetradecylaminoethyl-6,6-dimethyl-1-azonia-4-azacyclohept-7-en-5-one-1-propionate.

Elementary analysis: $C_{26}H_{49}O_3N_3$; Calculated (%)—C 69.14, H 10.94, N 9.30, Found (%)—C 69.16, H 10.96, N 9.33.

IR spectrum—1645 cm$^{-1}$

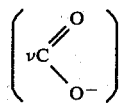

NMR spectrum—

$$\overset{+}{N}-\underset{\underset{CH_3}{|}}{C}HCOO^-$$

methyne proton 2.42 ppm ($\delta$, DSS standard, 50 MHz).

EXAMPLE 59

Into an apparatus similar to that in Example 1, were charged 339.5 g (1 mole) of N-(2-hydroxy)hexadecyldiethylenetriamine and 144.2 g (1 mole) of ethyl 2-formyl-2-methylpropionate. At 140° to 160° C., 18 g of water and 46 g of ethanol were distilled off to obtain 4-(2-hydroxyhexadecyl)aminoethyl-6,6-dimethyl-3-hydro-2H-1,4-diazepin-5-one.

Elementary analysis: $C_{25}H_{45}O_2N_3$; Calculated (%)—C 71.55, H 10.82, N 10.01, Found (%)—C 71.59, H 10.83, N 10.00.

Amine value—267.5 (theoretical 267.3)

IR spectrum—1615 cm$^{-1}$ ($\nu_{C=N}$), 1655 cm$^{-1}$ ($\nu_{C=O}$, amide).

Subsequently, to a solution of 419.7 g (1 mole) of 4-(2-hydroxyhexadecyl)aminoethyl-6,6-dimethyl-3-hydro-2H-1,4-diazepin-5-one dissolved in 300 g of tetrahydrofuran, was added a solution of 177.0 g (1 mole) of potassium monobromoacetate dissolved in 800 g of water. The acetate radical formation was effected at 60° to 70° C. to obtain 4-(2-hydroxyhexadecyl)aminoethyl-6,6-dimethyl-1-azonia-4-azacyclohept-7-en-5-one-1-acetate.

Elementary analysis: $C_{27}H_{47}O_4N_3$; Calculated (%)—C 67.89, H 9.92, N 8.79, Found (%)—C 67.91, H 9.90, N 8.81.

IR spectrum—1645 cm$^{-1}$

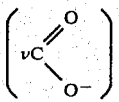

NMR spectrum—$N^+$-$CH_2COO^-$ proton 2.12 ppm ($\delta$, DSS standard, 50 MHz).

EXAMPLE 60

Into an apparatus similar to that in Example 1, were charged 313.5 g (1 mole) of N-monotetradecylaminoethylpropylenediamine and 158.2 g (1 mole) of isopropyl 2-formyl-2-methylpropionate. At 150° to 155° C., 18 g of water and 60 g of isopropyl alcohol were distilled off to obtain 1-tetradecylaminoethyl-3,3-dimethyl-6,7,8-trihydro-1,5-diazocin-5-one.

Elementary analysis: $C_{24}H_{47}ON_3$; Calculated (%)—C 73.32, H 12.04, N 10.67, Found (%)—C 73.30, H 12.00, N 10.69.

Amine value—285.1 (theoretical 285.1).

IR spectrum—1610 cm$^{-1}$ ($\nu_{C=N}$), 1660 cm$^{-1}$ ($\nu_{C=O}$, amide).

Subsequently, to a solution of 107.6 g (1 mole) of monochloropropionic acid dissolved in 700 g of water, was added dropwise 393.6 g (1 mole) of 1-tetradecylaminoethyl-3,3-dimethyl-6,7,8-trihydro-1,5-diazocin-5-one. After mixing at 70° to 80° C. and adding 56.1 g (1 mole) of potassium hydroxide, the reaction was allowed to proceed at the same temperature to obtain 1-tetradecylaminoethyl-3,3-dimethyl-1-aza-5-azoniacyclooct-4-en-2-one-5-propionate.

Elementary analysis: $C_{27}H_{51}O_3N_3$; Calculated (%)—C 69.64, H 11.04, N 9.02, Found (%)—C 69.60, H 11.03, N 9.04.

IR spectrum—1630 cm$^{-1}$

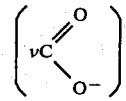

NMR spectrum—

$$\overset{+}{N}-\underset{\underset{CH_3}{|}}{C}HCOO^-$$

metyne proton 2.38 ppm ($\delta$, DSS standard, 50 MHz).

EXAMPLE 61

Into an apparatus similar to that in Example 1, were charged 353.5 g (1 mole) of N-mono(2-hydroxy)hexadecylaminoethylpropylenediamine and 172.2 g (1 mole) of butyl 2-formyl-2-methylpropionate. At 160° to 165° C. and under a reduced pressure of 70 mmHg, 18 g of water and 74 g of butanol were distilled off to obtain 1-(2-hydroxyhexadecyl)aminoethyl-3,3-dimethyl-6,7,8-trihydro-1,5-diazocin-5-one.

Elementary analysis: $C_{26}H_{47}O_2N_3$; Calculated (%)—C 72.01, H 10.93, N 9.68, Found (%)—C 71.98, H 10.90, N 9.68.

Amine value—258.9 (theoretical 258.7).

IR spectrum—1615 cm$^{-1}$ ($\nu_{C=N}$), 1655 cm$^{-1}$ ($\nu_{C=O}$, amide).

Subsequently, to a solution of 433.7 g (1 mole) of 1-(2-hydroxyhexadecyl)aminoethyl-3,3-dimethyl-6,7,8-trihydro-1,5-diazocin-5-one dissolved in 300 g of ethanol, was added a solution of 116.5 g (1 mole) of sodium monochloroacetate dissolved in 600 g of water. The acetate radical formation was effected at 60° to 70° C. to obtain 1-(2-hydroxyhexadecyl)aminoethyl-3,3-dimethyl-1-aza-5-azoniacyclooct-4-en-2-one-5-acetate.

Elementary analysis: $C_{28}H_{49}O_4N_3$; Calculated (%)—C 68.40, H 10.05, N 8.54, Found (%)—C 68.40, H 10.08, N 8.55.

IR spectrum—1640 cm$^{-1}$

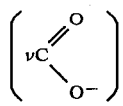

NMR spectrum—N$^+$-CH$_2$COO$^-$ proton 2.11 ppm (δ, DSS standard, 50 MHz).

EXAMPLE 62

Into an apparatus similar to that in Example 1, were charged 364.2 g (1 mole) of N-nonylphenylpoly(2 moles) oxyethyleneoxyethyl-1,3-propylene diamine and 130.1 g (1 mole) of methyl 2-formyl-2-methylpropionate. At 100° C. and under a reduced pressure of 100 mmHg, 18 g of water and 32 g of methanol were distilled off to obtain 1-nonylphenylpoly(2 moles)oxyethyleneoxyethyl-3,3-dimethyl-6,7,8-trihydro-1,5-diazocin-5-one.

Elementary analysis: $C_{27}H_{44}O_3N_2$; Calculated (%)—C 72.93, H 9.98, N 6.30, Found (%)—C 72.90, H 9.97, N 6.34.

Amine value—125.0 (theoretical 126.2).

IR spectrum—1620 cm$^{-1}$ ($\nu_{C=N}$), 1650 cm$^{-1}$ ($\nu_{C=O}$, amide).

Subsequently, to a solution of 161.0 g (1 mole) of sodium monobromoacetate dissolved in 500 g of water, was added dropwise 444.7 g (1 mole) of 1-nonylphenylpoly(2 moles)oxyethyleneoxyethyl-3,3-dimethyl-6,7,8-trihydro-1,5-diazocin-5-one. The acetate radical formation was effected at 60° to 70° C. to obtain 1-nonylphenylpoly(2 moles)oxyethyleneoxyethyl-3,3-dimethyl-1-aza-5-azoniacyclooct-4-en-2-one-5-acetate.

Elementary analysis: $C_{28}H_{46}O_5N_2$; Calculated (%)—C 68.53, H 9.46, N 5.71, Found (%)—C 68.57, H 9.48, N 5.71.

IR spectrum—1635 cm$^{-1}$

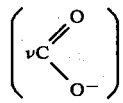

NMR spectrum—N$^+$-CH$_2$COO$^-$ proton 2.10 ppm (δ, DSS standard, 50 MHz).

EXAMPLE 63

Into an apparatus similar to that in Example 1, were charged 230.1 g (1 mole) of N-octoxypropylethylenediamine and 130.1 g (1 mole) of methyl 2-formyl-2-methylpropionate. At 130° to 135° C., 18 g of water and 32 g of methanol were distilled off to obtain 4-octoxypropyl-6,6-dimethyl-3-hydro-2H-1,4-diazepin-5-one.

Elementary analysis: $C_{18}H_{34}O_2N_2$; Calculated (%)—C 69.63, H 11.05, N 9.02, Found (%)—C 69.60, H 11.04, N 9.05.

Amine value—180.7 (theoretical 180.7).

IR spectrum—1610 cm$^{-1}$ ($\nu_{C=N}$), 1655 cm$^{-1}$ ($\nu_{C=O}$, amide).

Subsequently, to a solution of 116.5 g (1 mole) of sodium monochloroacetate dissolved in 600 g of water, was added dropwise 310.5 g (1 mole) of 4-octoxypropyl-6,6-dimethyl-3-hydro-2H-1,4-diazepin-5-one. The acetate radical formation was effected at 50° to 60° C. to obtain 4-oxtoxypropyl-6,6-dimethyl-1-azonia-4-azacyclohept-7-en-5-one-1-acetate.

Elementary analysis: $C_{20}H_{36}O_4N_2$; Calculated (%)—C 65.18, H 9.85, N 7.60, Found (%)—C 65.20, H 9.85, N 7.61.

IR spectrum—1635 cm$^{-1}$

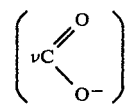

NMR spectrum—N$^+$-CH$_2$COO$^-$ proton 2.18 ppm (δ, DSS standard, 50 MHz).

EXAMPLE 64

Into an apparatus similar to that in Example 1, were charged 103.1 g (1 mole) of diethylenetriamine and 144.2 g (1 mole) of ethyl 2-formyl-2-methylpropionate. At 140° C., 18 g of water and 46 g of methanol were distilled off. Then, after addition of 312.5 g (1 mole) of methyl ricinoleate, amide formation was carried out at 170° to 180° C. under a reduced pressure of 70 mmHg to distil off 32 g of methanol, yielding 4-ricinolamidoethyl-6,6-dimethyl-3-hydro-2H-1,4-diazepin-5-one.

Elementary analysis: $C_{27}H_{49}O_3N_3$; Calculated (%)—C 69.94, H 10.65, N 9.06, Found (%)—C 69.98, H 10.66, N 9.05.

Amine value—120.6 (theoretical 121.0).

IR spectrum—1615 cm$^{-1}$ ($\nu_{C=N}$), 1660 cm$^{-1}$ ($\nu_{C=O}$, amide).

Subsequently, to a solution of 94.5 g (1 mole) of monochloroacetic acid dissolved in 500 g of water, was added dropwise 463.7 g (1 mole) of 4-ricinolamidoethyl-6,6-dimethyl-3-hydro-2H-1,4-diazepin-5-one. After mixing at 50° to 60° C. and adding 40.0 g (1 mole) of sodium hydroxide, the reaction was allowed to proceed at the same temperature to obtain 4-ricinolamidoethyl-6,6-dimethyl-1-azonia-4-azacyclohept-7-en-5-one-1-acetate.

Elementary analysis: $C_{29}H_{51}O_5N_3$; Calculated (%)—C 66.76, H 9.85, N 8.05, Found (%)—C 66.78, H, 9.85, N 8.05.

IR spectrum—1630 cm$^{-1}$

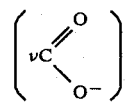

NMR spectrum—N$^+$-CH$_2$COO$^-$ proton 2.10 ppm (δ, DSS standard, 50 MHz).

EXAMPLE 65

Into an apparatus similar to that in Example 1, where charged 299.5 g (1 mole) of N-tetradecyldiethylenetriamine and 130.1 g (1 mole) of methyl 3-formyl-2-methylpropionate. At 145° to 150° C., 18 g of water and 32 g of methanol were distilled off to obtain 4-tetradecylaminoethyl-6-methyl-2,3,6,7-tetrahydro-1,4-diazocin-5-one.

Elementary analysis: $C_{23}H_{45}ON_3$; Calculated (%)—C 72.76, H 11.96, N 11.06, Found (%)—C 72.73, H 11.94, N 11.08.

Amine value—295.9 (theoretical 295.6).

IR spectrum—1615 cm$^{-1}$ ($\nu_{C=N}$), 1655 cm$^{-1}$ ($\nu_{C=O}$, amide).

Subsequently, to a solution of 107.6 g (1 mole) of monochloropropionic acid dissolved in 600 g of water, was added dropwise 379.6 g (1 mole) of 4-tetradecylaminoethyl-6-methyl-2,3,6,7-tetrahydro-1,4-diazocin-5-one. After mixing at 70° C. to 80° C. and adding 56.1 g (1 mole) of potassium hydroxide, the reaction was allowed to proceed at the same temperature to obtain 4-tetradecylaminoethyl-6-methyl-4-aza-1-azoniacyclooct-8-en-5-one-1-propionate.

Elementary analysis: $C_{26}H_{49}O_3N_3$; Calculated (%)—C 69.14, H 10.94, N 9.30, Found (%)—C 69.14, H 10.95, N 9.32.

IR spectrum—1640 cm$^{-1}$

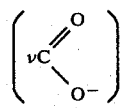

NMR spectrum—

$$\overset{+}{N}-\underset{\underset{CH_3}{|}}{CH}COO^-$$

methyne proton 2.40 ppm ($\delta$, DSS standard, 50 MHz).

EXAMPLE 66

Into an apparatus similar to that in Example 1, were charged 339.5 g (1 mole) of N-(2-hydroxy)hexadecyldiethylenetriamine and 144.2 g (1 mole) of ethyl 3-formyl-2-methylpropionate. At 140° to 160° C., 18 g of water and 46 g of ethanol were distilled off to obtain 4-(2-hydroxyhexadecyl)aminoethyl-6-methyl-2,3,6,7-tetrahydro-1,4-diazocin-5-one.

Elementary analysis: $C_{25}H_{45}O_2N_3$; Calculated (%)—C 71.55, H 10.82, N 10.01, Found (%)—C 71.51, H 10.80, N 10.04.

Amine value—267.7 (theoretical 267.3).

IR spectrum—1615 cm$^{-1}$ ($\nu_{C=N}$), 1660 cm$^{-1}$ ($\nu_{C=O}$, amide).

Subsequently, to a solution of 419.7 g (1 mole) of 4-(2-hydroxyhexadecyl)aminoethyl-6-methyl-2,3,6,7-tetrahydro-1,4-diazocin-5-one dissolved in 200 g of dioxane, was added a solution of 116.5 g (1 mole) of sodium monochloroacetate dissolved in 800 g of water. The acetate radical formation was effected at 60° to 70° C. to obtain 4-(2-hydroxyhexadecyl)aminoethyl-6-methyl-4-aza-1-azoniacyclooct-8-en-5-one-1-acetate.

Elementary analysis: $C_{27}H_{47}O_4N_3$; Calculated (%)—C 67.89, H 9.92, N 8.79, Found (%)—C 67.92, H 9.94, N 8.80.

IR spectrum—1645 cm$^{-1}$

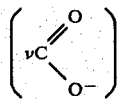

NMR spectrum—N$^+$-CH$_2$COO$^-$ proton 2.10 ppm ($\delta$, DSS standard, 50 MHz).

EXAMPLE 67

Into an apparatus similar to that in Example 1, were charged 338.5 g (1 mole) of N-methylbenzylpoly(2 moles)oxypropyleneoxypropylethylenediamine and 172.2 g (1 mole) of butyl 3-formyl-2-methylpropionate. At 150° to 160° C., 18 g of water and 74 g of butanol to obtain 4-methylbenzylpoly(2 moles)oxypropyleneoxypropyl-6-methyl-2,3,6,7-tetrahydro-1,4-diazocin-5-one.

Elementary analysis: $C_{24}H_{38}O_4N_2$; Calculated (%)—C 68.86, H 9.15, N 6.69, Found (%)—C 68.80, H 9.14, N 6.71.

Amine value—135.0 (theoretical 134.1).

IR spectrum—1610 cm$^{-1}$ ($\nu_{C=N}$), 1660 cm$^{-1}$ ($\nu_{C=O}$, amide).

Subsequently, to a solution of 116.5 g (1 mole) of sodium monochloroacetate dissolved in 600 g of water, was added dropwise 418.5 g (1 mole) of 4-methylbenzylpoly(2moles)oxypropyleneoxypropyl-6-methyl-2,3,6,7-tetrahydro-1,4-diazocin-5-one. The acetate radical formation was effected at 50° to 60° C. to obtain 4-methylbenzylpoly(2 moles)oxypropyleneoxypropyl-6-methyl-4-aza-1-azoniacyclooct-8-en-5-one-1-acetate.

Elementary analysis: $C_{26}H_{40}O_6N_2$; Calculated (%)—C 65.53, H 8.46, N 5.87, Found (%)—C 65.58, H 8.46, N 5.86.

IR spectrum—1630 cm$^{-1}$

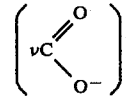

NMR spectrum—N$^+$-CH$_2$COO$^-$ proton 2.07 ppm ($\delta$, DSS standard, 50 MHz).

EXAMPLE 68

Into an apparatus similar to that in Example 1, were charged 118.2 g (1 mole) of N-hydroxypropylethylenediamine and 158.2 g (1 mole) of isopropyl 3-formyl-2-methylpropionate. From the apparatus, 18 g of water and 60 g of isopropyl alcohol were distilled off. Then, 340.5 g (1 mole) of behenic acid was charged and 18 g of water was distilled off at 180° C. and under a reduced pressure of 70 mmHg to obtain 4-behenoyloxypropyl-6-methyl-2,3,6,7-tetrahydro-1,4-diazocin-5-one.

Elementary analysis: $C_{32}H_{58}O_3N_2$; Calculated (%)—C 74.08, H 11.27, N 53.97, Found (%)—C 74.10, H 11.27, N 54.01.

Amine value—108.5 (theoretical 108.1).

IR spectrum—1610 cm$^{-1}$ ($\nu_{C=N}$), 1660 cm$^{-1}$ ($\nu_{C=O}$, amide), 1735 cm$^{-1}$ ($\nu_{C=O}$, ester).

Subsequently, to a solution of 518.1 g (1 mole) of 4-behenoyloxypropyl-6-methyl-2,3,6,7-tetrahydro-1,4-diazocin-5-one dissolved in 600 g of tetrahydrofuran, was added dropwise a solution of 116.5 g (1 mole) of sodium monochloroacetate dissolved in 600 g of water. The acetate radical formation was effected at 70° to 80° C. to obtain 4-behenoyloxypropyl-6-methyl-4aza-1-azoniacyclooct-8-en-5-one-1-acetate.

Elementary analysis: $C_{34}H_{60}O_5N_2$; Calculated (%)—C 70.79, H 10.49, N 4.85, Found (%)—C 70.78, H 10.47, N 4.85.

IR spectrum—1640 cm$^{-1}$

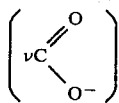

NMR spectrum—N+-CH₂COO⁻ proton 2.06 ppm (δ, DSS standard, 50 MHz).

EXAMPLE 69

Into an apparatus similar to that in Example 1, were charged 465.7 g (1 mole) of N-nonylphenoxy(2-hydroxy)propyltetraethylenepentamine and 144.2 g (1 mole) of ethyl 3-formyl-2-methylpropionate. At 120° to 130° C. and under a reduced pressure of 100 mmHg, 18 g of water and 46 g of ethanol were distilled off to obtain 4-nonylphenoxy(2-hydroxy)propylaminoethylaminoethylaminoethyl-6-methyl-2,3,6,7-tetrahydro-1,4-diazocin-5-one.

Elementary analysis: $C_{31}H_{55}O_3N_5$; Calculated (%)—C 68.22, H 10.15, N 12.83, Found (%)—C 68.20, H 10.15, N 12.80.

Amine value—410.0 (theoretical 411.2).

IR spectrum—1610 cm⁻¹ ($\nu_{C=N}$), 1655 cm⁻¹ ($\nu_{C=O}$, amide).

Subsequently, to a solution of 177.0 g (1 mole) of potassium monobromoacetate dissolved in 1,000 g of water, was added dropwise 545.7 g (1 mole) of 4-nonylphenoxy(2-hydroxy)propylaminoethylaminoethylaminoethyl-6-methyl-2,3,6,7-tetrahydro-1,4-diazocin-5-one. The acetate radical formation was effected at 55° to 60° C. to obtain 4-nonylphenoxy(2-hydroxy)propylaminoethylaminoethylaminoethyl-6-methyl-4-aza-1-azoniacyclooct-8-en-5-one-1-acetate.

Elementary analysis: $C_{33}H_{57}O_5N_5$; Calculated (%)—C 65.63, H 9.52, N 11.59, Found (%)—C 65.50, H 9.49, N 11.59.

IR spectrum—1645 cm⁻¹

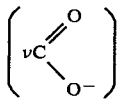

NMRS spectrum—N+-CH₂COO⁻ proton 2.11 ppm (δ, DSS standard, 50 MHz).

EXAMPLE 70

Into an apparatus similar to that in Example 1, were charged 429.6 g (1 mole) of a monotridecoxyethyl derivative of a 1,3-propanediaminepoly(3 moles on the average)ethyleneimine adduct and 130.1 g (1 mole) of methyl 3-formyl-2-methylpropionate. At 150° to 155° C., 18 g of water and 32 g of methanol were distilled off to synthesize an N-alkylazaalkenelactam.

Elementary analysis: $C_{29}H_{59}O_2N_5$; Calculated (%)—C 68.32, H 11.67, N 13.73, Found (%)—C 68.36, H 11.69, N 13.70.

Amine value—439.1 (theoretical 440.2).

IR spectrum—1610 cm⁻¹ ($\nu_{C=O}$), 1650 cm⁻¹ ($\nu_{C=O}$, amide).

Subsequently, to a solution of 116.5 g (1 mole) of sodium monochloroacetate dissolved in 1,000 g of water, was added dropwise 509.8 g (1 mole) of the formed N-alkylazaalkenelactam. The reaction was allowed to proceed at 60° to 70° C. to obtain the compound having an acetate radical.

Elementary analysis: $C_{31}H_{61}O_4N_5$; Calculated (%)—C 65.57, H 10.83, N 12.33, Found (%)—C 65.57, H 10.80, N 12.33.

IR spectrum—1635 cm⁻¹

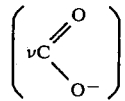

NMR spectrum—N+-CH₂COO proton 2.11 ppm (δ, DSS standard, 50 MHz).

EXAMPLE 71

Below are described the antibacterial activities of the compounds in the compositions according to this invention. The results of antibacterial activity tests on the N-alkyl-substituted azaalkenelactams and their derivatives having a carboxylate radical of Examples 1 to 70 were as shown in Tables 1 to 3.

The testing method complied with the standard method of Japan Sociaty of Chemotherapy. Aqueous solutions of each compound in distilled water in various concentrations were added to the following bacteria cultivated in heart infusion agar media at 37° C. and the minimum concentration of the compound to inhibit completely the growth of test bacteria in 24 hours (hereinafter referred to as MIC) was examined: *Escherichia coli* NIHJ, *Staphylococcus aureus* FDA 209P, *Desulfovibrio desulfuricans* IFO 3699, *Pseudomonas aeruginosa* IFO 3445, *Bacillus subtilis* ATCC 6633, *Pasteurella multocida, almonella typhimurium, Staphylococcus epidermidis,* and *Streptococcus faecalis,* wherein *Desulfovibrio desulfuricans* is a bacterium which generates hydrogen sulfide and, for this reason, acts to cause corrosion of metals.

EXAMPLE 72

In Tables 4 and 5, are further shown the results of tests for the metal corrosion inhibiting performance of the systems comprising an automobile brake fluid A of the following composition and, incorporated therein, each 0.25% by weight of N-alkyl-substituted azaalkenelactams or their derivatives having a carboxylate radical obtained in Examples 1 to 70.

Brake fluid composition A;
  Trioxyethylene glycol monomethyl ether—35 parts
  Trioxyethylene glycol monoethyl ether—20 parts
  Trioxyethylene glycol monobutyl ether—20 parts
  Poly(20 moles on the average)oxyethylene glycol monomethyl ether—15 parts
  Poly(10 moles on the average)oxyethylene-poly(10 moles on the average)oxypropylene glycol monoethyl ether—10 parts The testing method conformed to Japanese Industrial Standards JIS K 2233: a series of metal plates of tinplate, steel, aluminum, cast iron, brass and copper connected to each other in the order indicated was immersed in the brake fluid system being tested, then left standing at 100°±2° C. for 120±2 hours and the weight difference per unit area before and after the test was examined.

As for the reference substances, laurylbutylamine and oleylaminopropyloleamide were selected for the N-alkyl-substituted azaalkenelactam, and lauryldimethylbetaine and 1-hydroxyethyl-2-undecylimidazolineum-betaine were selected for the derivatives having an organic acid, e.g. a carboxylate radical of said lactam.

These were subjected to the antibacterial activity test and the metal corrosion test in a similar manner to that described above.

TABLE 1

Antibacterial Activity of Azaalkenelactams with Long chain hydrocarbon radical

| Sample (Azaalkenelactam) | MIC (μg/ml) | | |
|---|---|---|---|
| | Esherichia coli HIHJ | Staphylococcus aureus FDA209P | Desulfovibrio desulfuricans IFO 13699 |
| Example 1 | 1600 | 50 | 6.25 |
| Example 2 | 25 | 12.5 | 12.5 |
| Example 3 | 1600 | 50 | 6.25 |
| Example 4 | 800 | 25 | 12.5 |
| Example 5 | 3200 | 12.5 | 6.25 |
| Example 6 | 50 | 12.5 | 25 |
| Example 7 | 200 | 12.5 | 12.5 |
| Example 8 | 800 | 50 | 50 |
| Example 9 | 25 | 12.5 | 6.25 |
| Example 10 | 1600 | 50 | 6.25 |
| Example 11 | 1600 | 100 | 6.25 |
| Example 12 | 1600 | 100 | 12.5 |
| Example 13 | 1600 | 100 | 12.5 |
| Example 14 | 1600 | 100 | 12.5 |
| Example 15 | 1600 | 50 | 6.25 |
| Example 16 | 50 | 100 | 25 |
| Example 17 | 1600 | 50 | 25 |
| Example 18 | 1600 | 100 | 12.5 |
| Example 19 | 400 | 50 | 25 |
| Example 20 | 800 | 50 | 12.5 |
| Example 21 | 800 | 50 | 25 |
| Example 22 | 800 | 25 | 12.5 |
| Example 23 | 25 | 25 | 50 |
| Example 24 | 800 | 200 | 25 |
| Example 25 | 1600 | 200 | 50 |
| Example 26 | 50 | 50 | 12.5 |
| Example 27 | 25 | 12.5 | 6.25 |
| Example 28 | 25 | 25 | 12.5 |
| Example 29 | 25 | 6.25 | 3.12 |
| Example 30 | 25 | 12.5 | 3.12 |
| Example 31 | 400 | 50 | 50 |
| Example 32 | 800 | 200 | 25 |
| Example 33 | 400 | 25 | 25 |
| Example 34 | 25 | 3.12 | 3.12 |
| Example 35 | 6.25 | 1.56 | 1.56 |
| Example 36 | 50 | 12.5 | 25 |
| Example 37 | 25 | 6.25 | 6.25 |
| Example 38 | 50 | 12.5 | 25 |
| Example 39 | 200 | 25 | 50 |
| Example 40 | 6.25 | 1.56 | 1.56 |
| Example 41 | 25 | 3.12 | 3.12 |
| Example 42 | 400 | 12.5 | 6.25 |
| Example 43 | 400 | 12.5 | 12.5 |
| Example 44 | 800 | 50 | 25 |
| Example 45 | 800 | 100 | 50 |
| Example 46 | 25 | 6.25 | 6.25 |
| Example 47 | 200 | 50 | 50 |
| Example 48 | 12.5 | 3.12 | 3.12 |
| Example 49 | 25 | 3.12 | 3.12 |
| Example 50 | 50 | 25 | 50 |
| Example 51 | 100 | 25 | 12.5 |
| Example 52 | 100 | 100 | 50 |
| Example 53 | 6.25 | 1.56 | 3.12 |
| Example 54 | 6.25 | 6.25 | 6.25 |
| Example 55 | 200 | 100 | 50 |
| Example 56 | 100 | 200 | 50 |
| Example 57 | 100 | 100 | 12.5 |
| Example 58 | 6.25 | 3.12 | 3.12 |
| Example 59 | 25 | 6.25 | 3.12 |
| Example 60 | 12.5 | 6.25 | 6.25 |
| Example 61 | 25 | 6.25 | 6.25 |
| Example 62 | 200 | 100 | 50 |
| Example 63 | 400 | 100 | 50 |
| Example 64 | 400 | 200 | 25 |
| Example 65 | 12.5 | 3.12 | 6.25 |
| Example 66 | 25 | 12.5 | 12.5 |
| Example 67 | 400 | 200 | 50 |
| Example 68 | 200 | 100 | 25 |
| Example 69 | 200 | 200 | 50 |
| Example 70 | 200 | 100 | 25 |
| Laurylbutylamide | 10000 or more | 10000 or more | 400 |
| Oleylaminopropyl | 10000 or more | 10000 or more | 100 |

TABLE 1-continued

Antibacterial Activity of Azaalkenelactams with Long chain hydrocarbon radical

| Sample (Azaalkenelactam) | MIC (μg/ml) | | |
|---|---|---|---|
| | Esherichia coli HIHJ | Staphylococcus aureus FDA209P | Desulfovibrio desulfuricans IFO 13699 |
| oleamide | | | |

TABLE 2

Antibacterial Activity of Derivatives having a carboxylate radical of Azaalkenelactams with long chain hydrocarbon radical

| Sample | | MIC (μg/ml) | | |
|---|---|---|---|---|
| | | Esherichia coli NIHJ | Staphylococcus aureus FDA 209P | Desulfovibrio desulfuricans IFO 13699 |
| Example 1, | Compound having an acetate radical | 3200 | 50 | 12.5 |
| Example 2, | Compound having an acetate radical | 100 | 50 | 12.5 |
| Example 3, | Compound having an acetate radical | 3200 | 100 | 12.5 |
| Example 4, | Compound having an acetate radical | 800 | 12.5 | 12.5 |
| Example 5, | Compound having an acetate radical | 3200 | 100 | 12.5 |
| Example 6, | Compound having an acetate radical | 200 | 25 | 25 |
| Example 7, | Compound having an acetate radical | 200 | 12.5 | 25 |
| Example 8, | Compound having an acetate radical | 1600 | 50 | 50 |
| Example 9, | Compound having an acetate radical | 100 | 50 | 12.5 |
| Example 10, | Compound having an acetate radical | 3200 | 25 | 12.5 |
| Example 11, | Compound having an acetate radical | 3200 | 50 | 25 |
| Example 12, | Compound having an acetate radical | 3200 | 400 | 25 |
| Example 13, | Compound having an acetate radical | 3200 | 200 | 25 |
| Example 14, | Compound having an acetate radical | 3200 | 400 | 25 |
| Example 15, | Compound having an acetate radical | 3200 | 200 | 12.5 |
| Example 16, | Compound having an acetate radical | 100 | 400 | 50 |
| Example 17, | Compound having an acetate radical | 3200 | 100 | 50 |
| Example 18, | Compound having an acetate radical | 3200 | 100 | 25 |
| Example 19, | Compound having an acetate radical | 800 | 50 | 50 |
| Example 20, | Compound having an acetate radical | 1600 | 50 | 25 |
| Example 21, | Compound having an acetate radical | 1600 | 50 | 25 |
| Example 22, | Compound having an acetate radical | 3200 | 12.5 | 12.5 |
| Example 23, | Compound having an acetate radical | 100 | 800 | 50 |
| Example 24, | Compound having an acetate radical | 3200 | 800 | 50 |
| Example 25, | Compound having an acetate radical | 3200 | 100 | 50 |
| Example 26, | Compound having an acetate radical | 200 | 100 | 6.25 |
| Example 27, | Compound having an acetate radical | 100 | 25 | 6.25 |
| Example 28, | Compound having an acetate radical | 100 | 50 | 12.5 |
| Example 29, | Compound having an acetate radical | 50 | 25 | 3.12 |
| Example 30, | Compound having an acetate radical | 50 | 25 | 6.25 |
| Example 31, | Compound having an acetate radical | 800 | 100 | 25 |
| Example 32, | Compound having an acetate radical | 800 | 100 | 50 |

TABLE 2-continued

Antibacterial Activity of Derivatives having a carboxylate radical of Azaalkenelactams with long chain hydrocarbon radical

| | Sample | MIC (μg/ml) | | |
|---|---|---|---|---|
| | | *Esherichia coli* NIHJ | *Staphylococcus aureus* FDA 209P | *Desulfovibrio desulfuricans* IFO 13699 |
| Example 33, | Compound having a propionate radical | 800 | 25 | 12.5 |
| Example 34, | Compound having an acetate radical | 100 | 12.5 | 6.25 |
| Example 35, | Compound having an acetate radical | 100 | 3.12 | 3.12 |
| Example 36, | Compound having an acetate radical | 100 | 12.5 | 50 |
| Example 37, | Compound having a propionate radical | 100 | 6.25 | 6.25 |
| Example 38, | Compound having an acetate radical | 100 | 12.5 | 25 |
| Example 39, | Compound having an acetate radical | 400 | 50 | 50 |
| Example 40, | Compound having an acetate radical | 100 | 6.25 | 6.25 |
| Example 41, | Compound having an acetate radical | 100 | 12.5 | 3.12 |
| Example 42, | Compound having an acetate radical | 800 | 25 | 25 |
| Example 43, | Compound having an acetate radical | 800 | 25 | 25 |
| Example 44, | Compound having an acetate radical | 1600 | 50 | 25 |
| Example 45, | Compound having an acetate radical | 1600 | 100 | 50 |
| Example 46, | Compound having an acetate radical | 50 | 12.5 | 6.25 |
| Example 47, | Compound having an acetate radical | 200 | 50 | 50 |
| Example 48, | Compound having a propionate radical | 100 | 6.25 | 6.25 |
| Example 49, | Compound having an acetate radical | 100 | 12.5 | 6.25 |
| Example 50, | Compound having an acetate radical | 100 | 50 | 50 |
| Example 51, | Compound having an acetate radical | 100 | 50 | 25 |
| Example 52, | Compound having an acetate radical | 400 | 200 | 50 |
| Example 53, | Compound having an acetate radical | 100 | 3.12 | 6.25 |
| Example 54, | Compound having an acetate radical | 100 | 12.5 | 6.25 |
| Example 55, | Compound having an acetate radical | 400 | 200 | 50 |
| Example 56, | Compound having a propionate radical | 200 | 400 | 50 |
| Example 57, | Compound having an acetate radical | 200 | 100 | 12.5 |
| Example 58, | Compound having a propionate radical | 100 | 6.25 | 6.25 |
| Example 59, | Compound having an acetate radical | 200 | 12.5 | 6.25 |
| Example 60, | Compound having a propionate radical | 100 | 12.5 | 6.25 |
| Example 61, | Compound having an acetate radical | 100 | 12.5 | 12.5 |
| Example 62, | Compound having an acetate radical | 400 | 100 | 50 |
| Example 63, | Compound having an acetate radical | 800 | 200 | 50 |
| Example 64, | Compound having an acetate radical | 1600 | 400 | 50 |
| Example 65, | Compound having a propionate radical | 100 | 6.25 | 6.25 |
| Example 66, | Compound having an acetate radical | 100 | 25 | 25 |
| Example 67, | Compound having an acetate radical | 800 | 400 | 25 |
| Example 68, | Compound having an acetate radical | 800 | 200 | 25 |
| Example 69, | Compound having an acetate radical | 400 | 200 | 50 |
| Example 70, | Compound having an | 400 | 200 | 25 |

TABLE 2-continued

Antibacterial Activity of Derivatives having a carboxylate radical of Azaalkenelactams with long chain hydrocarbon radical

| Sample | MIC (μg/ml) | | |
|---|---|---|---|
| | Esherichia coli NIHJ | Staphylococcus aureus FDA 209P | Desulfovibrio desulfuricans IFO 13699 |
| acetate radical | | | |
| Lauryldimethylbetaine | 10000 or more | 10000 or more | 1600 |
| 1-hydroxyethyl-2-undecylimidazoliniumbetaine | 10000 or more | 3600 | 400 |

TABLE 3

Antibacterial activity of Azaalkenelactams with long chain hydrocarbon radical and their derivatives having an organic acid radical

| | | MIC (μg/ml) | | | | | | |
|---|---|---|---|---|---|---|---|---|
| | Sample | aruginosa | Pseudomonas subtilis IFO 3443 | Bacillus multo- ATCC 6633 | Pasteurella typhicida | Salmonella epidernurium | Staphylococcus coccus midis | Streptofaecalis |
| Example 2, | Azaalkenelactam | | 100 | 12.5 | <1.56 | 3.12 | 1.56 | 12.5 |
| Example 9, | Azaalkenelactam | | 100 | 25 | 3.12 | 6.25 | 6.25 | 12.5 |
| Example 9, | Compound having an acetate radical | | 200 | 50 | <1.56 | 6.25 | 12.5 | 12.5 |
| Example 29, | Azaalkenelactam | | 100 | 3.12 | <1.56 | 3.12 | 1.56 | 6.25 |
| Example 34, | Azaalkenelactam | | 100 | 3.12 | <1.56 | 3.12 | <1.56 | 6.25 |
| Example 35, | Azaalkenelactam | | 54 | 3.12 | <1.56 | 1.56 | <1.56 | 3.12 |
| Example 35, | Compound having an acetate radical | | 100 | 12.5 | 3.12 | 6.25 | 3.12 | 6.25 |
| Example 40, | Azaalkenelactam | | 50 | 3.12 | <1.56 | 3.12 | <1.56 | 3.12 |
| Example 41, | Azaalkenelactam | | 100 | 3.12 | <1.56 | 3.12 | 1.56 | 6.25 |
| Example 48, | Azaalkenelactam | | 50 | 6.25 | <1.56 | 3.12 | 1.56 | 6.25 |
| Example 49, | Azaalkenelactam | | 200 | 3.12 | <1.56 | 3.12 | 1.56 | 6.25 |
| Example 53, | Azaalkenelactam | | 100 | 3.12 | <1.56 | 3.12 | 1.56 | 6.25 |
| Example 54, | Azaalkenelactam | | 200 | 3.12 | <1.56 | 3.12 | 1.56 | 6.25 |
| Example 58, | Azaalkenelactam | | 50 | 3.12 | <1.56 | 1.56 | <1.56 | 3.12 |
| Example 59, | Azaalkenelactam | | 100 | 3.12 | <1.56 | 3.12 | 1.56 | 6.25 |
| Example 60, | Azaalkenelactam | | 100 | 3.12 | <1.56 | 3.12 | 1.56 | 6.25 |
| Example 61, | Azaalkenelactam | | 200 | 3.12 | <1.56 | 3.12 | 1.56 | 6.25 |
| Example 65, | Azaalkenelactam | | 100 | 3.12 | <1.56 | 3.12 | 1.56 | 6.25 |
| Example 66, | Azaalkenelactam | | 200 | 6.25 | <1.56 | 3.12 | 1.56 | 6.25 |

TABLE 4

Metal corrosion inhibiting performance of azaalkenelactams with long chain hydrocarbon radical in brake fluid A

| | | Test metal | | | | | |
|---|---|---|---|---|---|---|---|
| | Sample added | Tin-plate Weight change | Steel Weight change | Aluminum Weight change | Cast iron Weight change | Brass Weight change | Copper Weight change |
| | Blanc (Brake fluid composition A) | −0.15 mg/cm$^2$ | −0.20 mg/cm$^2$ | +0.07 mg/cm$^2$ | −0.14 mg/cm$^2$ | −0.20 mg/cm$^2$ | +0.18 mg/cm$^2$ |
| Example 1, | N-Alkyl substituted azaalkenelactam | 0 | −0.01 | +0.02 | −0.02 | 0 | +0.02 |
| Example 2, | N-Alkyl substituted aza- | 0 | −0.01 | 0 | 0 | −0.01 | 0 |

TABLE 4-continued

Metal corrosion inhibiting performance of azaalkenelactams with long chain hydrocarbon radical in brake fluid A

| Sample added Blanc (Brake fluid composition A) | | Test metal | | | | | |
|---|---|---|---|---|---|---|---|
| | | Tin-plate Weight change −0.15 mg/cm² | Steel Weight change −0.20 mg/cm² | Aluminum Weight change +0.07 mg/cm² | Cast iron Weight change −0.14 mg/cm² | Brass Weight change −0.20 mg/cm² | Copper Weight change +0.18 mg/cm² |
| Example 3, | N-Alkyl substituted azaalkenelactam | 0 | 0 | +0.01 | −0.02 | −0.01 | +0.01 |
| Example 4, | N-Alkyl substituted azaalkenelactam | −0.01 | 0 | 0 | −0.01 | −0.01 | +0.02 |
| Example 5, | N-Alkyl substituted azaalkenelactam | −0.01 | −0.01 | 0 | 0 | −0.02 | +0.02 |
| Example 6, | N-Alkyl substituted azaalkenelactam | 0 | −0.01 | +0.02 | −0.01 | 0 | +0.03 |
| Example 7, | N-Alkyl substituted azaalkenelactam | 0 | 0 | +0.03 | −0.01 | −0.02 | +0.01 |
| Example 8, | N-Alkyl substituted azaalkenelactam | −0.01 | −0.02 | +0.01 | −0.02 | −0.01 | +0.01 |
| Example 9, | N-Alkyl substituted azaalkenelactam | 0 | 0 | 0 | −0.01 | −0.02 | +0.03 |
| Example 10, | N-Alkyl substituted azaalkenelactam | −0.02 | −0.01 | 0 | 0 | −0.02 | +0.01 |
| Example 11, | N-Alkyl substituted azaalkenelactam | 0 | −0.01 | +0.01 | −0.02 | −0.03 | +0.02 |
| Example 12, | N-Alkyl substituted azaalkenelactam | 0 | −0.01 | 0 | 0 | −0.02 | +0.02 |
| Example 13, | N-Alkyl substituted azaalkenelactam | 0 | −0.02 | +0.03 | −0.03 | −0.02 | +0.01 |
| Example 14, | N-Alkyl substituted azaalkenelactam | −0.01 | 0 | −0.01 | −0.01 | −0.01 | +0.01 |
| Example 15, | N-Alkyl substituted azaalkenelactam | 0 | 0 | 0 | −0.01 | 0 | +0.01 |
| Example 16, | N-Alkyl substituted azaalkenelactam | −0.02 | −0.01 | +0.01 | 0 | −0.01 | +0.01 |
| Example 17, | N-Alkyl substituted azaalkenelactam | 0 | −0.01 | +0.01 | −0.01 | −0.01 | +0.01 |
| Example 18, | N-Alkyl substituted azaalkenelactam | −0.01 | 0 | 0 | −0.01 | −0.03 | +0.03 |
| Example 19, | N-Alkyl substituted azaalkenelactam | −0.02 | −0.02 | +0.01 | −0.02 | 0 | +0.01 |
| Example 20, | N-Alkyl substituted azaalkenelactam | −0.01 | −0.02 | +0.02 | −0.01 | −0.01 | +0.01 |
| Example 21, | N-Alkyl substituted azaalkenelactam | 0 | −0.02 | +0.01 | 0 | −0.01 | +0.02 |
| Example 22, | N-Alkyl substituted azaalkenelactam | 0 | 0 | +0.01 | −0.03 | −0.01 | +0.01 |
| Example 23, | N-Alkyl substituted azaalkenelactam | 0 | −0.01 | 0 | −0.01 | −0.03 | +0.03 |
| Example 24, | N-Alkyl substituted azaalkenelactam | −0.01 | −0.01 | +0.01 | 0 | −0.02 | +0.01 |
| Example 25, | N-Alkyl substituted azaalkenelactam | 0 | −0.01 | 0 | −0.01 | −0.03 | +0.03 |
| Example 26, | N-Alkyl substituted aza- | 0 | −0.01 | +0.01 | −0.02 | −0.01 | +0.03 |

TABLE 4-continued

Metal corrosion inhibiting performance of azaalkenelactams with long chain hydrocarbon radical in brake fluid A

| Sample added Blanc (Brake fluid composition A) | | Test metal | | | | | |
|---|---|---|---|---|---|---|---|
| | | Tin-plate Weight change −0.15 mg/cm² | Steel Weight change −0.20 mg/cm² | Aluminum Weight change +0.07 mg/cm² | Cast iron Weight change −0.14 mg/cm² | Brass Weight change −0.20 mg/cm² | Copper Weight change +0.18 mg/cm² |
| Example 27, | N-Alkyl substituted azaalkenelactam | −0.01 | −0.01 | +0.02 | 0 | −0.03 | +0.01 |
| Example 28, | N-Alkyl substituted azaalkenelactam | −0.01 | −0.01 | 0 | −0.01 | −0.03 | +0.02 |
| Example 29, | N-Alkyl substituted azaalkenelactam | −0.01 | 0 | +0.01 | −0.01 | −0.01 | 0 |
| Example 30, | N-Alkyl substituted azaalkenelactam | 0 | −0.01 | +0.01 | −0.02 | −0.02 | +0.02 |
| Example 31, | N-Alkyl substituted azaalkenelactam | −0.01 | −0.02 | +0.01 | −0.01 | −0.03 | +0.01 |
| Example 32, | N-Alkyl substituted azaalkenelactam | −0.02 | −0.02 | +0.03 | 0 | −0.03 | +0.02 |
| Example 33, | N-Alkyl substituted azaalkenelactam | −0.01 | 0 | +0.01 | −0.01 | −0.02 | +0.02 |
| Example 34, | N-Alkyl substituted azaalkenelactam | 0 | −0.01 | 0 | −0.01 | −0.01 | +0.01 |
| Example 35, | N-Alkyl substituted azaalkenelactam | 0 | −0.01 | 0 | −0.01 | 0 | +0.01 |
| Example 36, | N-Alkyl substituted azaalkenelactam | −0.01 | −0.02 | +0.02 | −0.01 | −0.02 | +0.02 |
| Example 37, | N-Alkyl substituted azaalkenelactam | −0.01 | 0 | +0.01 | −0.01 | −0.03 | +0.03 |
| Example 38, | N-Alkyl substituted azaalkenelactam | −0.01 | 0 | +0.02 | −0.02 | −0.02 | +0.01 |
| Example 39, | N-Alkyl substituted azaalkenelactam | 0 | −0.01 | +0.02 | −0.01 | −0.02 | +0.02 |
| Example 40, | N-Alkyl substituted azaalkenelactam | −0.01 | −0.01 | +0.01 | −0.01 | 0 | 0 |
| Example 41, | N-Alkyl substituted azaalkenelactam | −0.01 | −0.01 | 0 | −0.01 | 0 | +0.01 |
| Example 42, | N-Alkyl substituted azaalkenelactam | −0.02 | −0.01 | +0.01 | 0 | −0.02 | +0.01 |
| Example 43, | N-Alkyl substituted azaalkenelactam | −0.01 | 0 | +0.01 | −0.02 | −0.02 | +0.01 |
| Example 44, | N-Alkyl substituted azaalkenelactam | 0 | −0.01 | +0.02 | −0.01 | −0.02 | +0.03 |
| Example 45, | N-Alkyl substituted azaalkenelactam | −0.02 | −0.02 | +0.01 | −0.02 | −0.02 | +0.03 |
| Example 46, | N-Alkyl substituted azaalkenelactam | 0 | −0.01 | +0.01 | −0.02 | −0.01 | +0.01 |
| Example 47, | N-Alkyl substituted azaalkenelactam | −0.01 | 0 | +0.01 | −0.02 | −0.02 | +0.02 |
| Example 48, | N-Alkyl substituted azaalkenelactam | 0 | −0.01 | +0.01 | −0.01 | −0.01 | 0 |
| Example 49, | N-Alkyl substituted azaalkenelactam | 0 | −0.01 | 0 | −0.01 | −0.01 | +0.01 |
| Example 50, | N-Alkyl substituted aza- | −0.02 | −0.02 | +0.01 | 0 | −0.02 | +0.02 |

TABLE 4-continued

Metal corrosion inhibiting performance of azaalkenelactams with long chain hydrocarbon radical in brake fluid A

| Sample added Blanc (Brake fluid composition A) | | Test metal | | | | | |
|---|---|---|---|---|---|---|---|
| | | Tin-plate Weight change −0.15 mg/cm$^2$ | Steel Weight change −0.20 mg/cm$^2$ | Aluminum Weight change +0.07 mg/cm$^2$ | Cast iron Weight change −0.14 mg/cm$^2$ | Brass Weight change −0.20 mg/cm$^2$ | Copper Weight change +0.18 mg/cm$^2$ |
| Example 51, | N-Alkyl substituted azaalkenelactam | −0.02 | −0.02 | 0 | −0.01 | −0.03 | +0.02 |
| Example 52, | N-Alkyl substituted azaalkenelactam | 0 | −0.01 | +0.01 | −0.02 | −0.02 | +0.02 |
| Example 53, | N-Alkyl substituted azaalkenelactam | −0.01 | 0 | +0.01 | −0.01 | −0.01 | 0 |
| Example 54, | N-Alkyl substituted azaalkenelactam | −0.01 | 0 | 0 | −0.01 | −0.01 | +0.01 |
| Example 55, | N-Alkyl substituted azaalkenelactam | 0 | −0.01 | +0.02 | −0.02 | −0.01 | +0.01 |
| Example 56, | N-Alkyl substituted azaalkenelactam | −0.02 | −0.01 | +0.02 | −0.02 | −0.02 | +0.01 |
| Example 57, | N-Alkyl substituted azaalkenelactam | −0.01 | −0.01 | +0.01 | −0.02 | −0.03 | +0.02 |
| Example 58, | N-Alkyl substituted azaalkenelactam | 0 | −0.01 | 0 | −0.01 | −0.01 | +0.01 |
| Example 59, | N-Alkyl substituted azaalkenelactam | −0.01 | 0 | +0.01 | 0 | −0.01 | +0.01 |
| Example 60, | N-Alkyl substituted azaalkenelactam | −0.01 | 0 | 0 | −0.01 | −0.01 | +0.01 |
| Example 61, | N-Alkyl substituted azaalkenelactam | 0 | −0.01 | +0.01 | −0.01 | 0 | +0.01 |
| Example 62, | N-Alkyl substituted azaalkenelactam | −0.01 | −0.02 | +0.02 | −0.02 | −0.02 | +0.02 |
| Example 63, | N-Alkyl substituted azaalkenelactam | −0.02 | −0.01 | +0.03 | −0.02 | −0.01 | +0.02 |
| Example 64, | N-Alkyl substituted azaalkenelactam | −0.01 | −0.01 | +0.02 | −0.02 | −0.02 | +0.02 |
| Example 65, | N-Alkyl substituted azaalkenelactam | 0 | −0.01 | 0 | −0.01 | −0.01 | −0.01 |
| Example 66, | N-Alkyl substituted azaalkenelactam | 0 | 0 | +0.01 | −0.01 | −0.01 | +0.01 |
| Example 67, | N-Alkyl substituted azaalkenelactam | −0.01 | −0.01 | +0.01 | −0.02 | −0.02 | +0.02 |
| Example 68, | N-Alkyl substituted azaalkenelactam | −0.01 | −0.02 | +0.01 | −0.02 | −0.01 | +0.02 |
| Example 69, | N-Alkyl substituted azaalkenelactam | −0.02 | −0.02 | +0.01 | −0.02 | −0.02 | +0.03 |
| Example 70, | N-Alkyl substituted azaalkenelactam | −0.01 | −0.01 | +0.02 | −0.01 | −0.01 | +0.02 |
| Laurylbutyramide | | −0.06 | −0.09 | +0.06 | −0.08 | −0.12 | +0.07 |
| Oleylaminopropylamide | | −0.04 | −0.07 | +0.05 | −0.04 | −0.10 | +0.11 |

TABLE 5

Metal corrosion inhibiting performance of derivatives having a carboxylate radical of azaalkenelactams with long chain hydrocarbon radical in brake fluid composition A

| Sample added Blanc (Brake fluid composition A) | | Test metal | | | | | |
|---|---|---|---|---|---|---|---|
| | | Tin plate Weight change −0.15 mg/cm$^2$ | Steel Weight change −0.20 mg/cm$^2$ | Aluminum Weight change +0.07 mg/cm$^2$ | Cast iron Weight change −0.14 mg/cm$^2$ | Brass Weight change −0.20 mg/cm$^2$ | Copper Weight change +0.18 mg/cm$^2$ |
| Example 1, | Compound having an acetate radical | −0.03 | −0.01 | 0 | −0.04 | +0.01 | 0 |
| Example 2, | Compound having an acetate radical | −0.02 | −0.02 | +0.01 | −0.01 | −0.03 | −0.04 |
| Example 3, | Compound having an acetate radical | −0.01 | −0.01 | +0.01 | 0 | 0 | 0 |
| Example 4, | Compound having an acetate radical | −0.01 | −0.03 | +0.01 | −0.03 | 0 | 0 |
| Example 5, | Compound having an acetate radical | −0.01 | −0.02 | 0 | −0.01 | 0 | 0 |
| Example 6, | Compound having an acetate radical | −0.02 | −0.01 | 0 | 0 | −0.01 | −0.01 |
| Example 7, | Compound having an acetate radical | −0.02 | −0.03 | +0.01 | −0.02 | −0.01 | 0 |
| Example 8, | Compound having an acetate radical | −0.02 | −0.03 | +0.01 | 0 | −0.01 | +0.01 |
| Example 9, | Compound having an acetate radical | −0.03 | −0.03 | +0.01 | −0.02 | −0.01 | 0 |
| Example 10, | Compound having an acetate radical | −0.01 | −0.01 | 0 | −0.01 | 0 | 0 |
| Example 11, | Compound having an acetate radical | −0.02 | −0.02 | +0.01 | −0.02 | 0 | −0.01 |
| Example 12, | Compound having an acetate radical | −0.02 | −0.01 | 0 | −0.01 | −0.01 | 0 |
| Example 13, | Compound having an acetate radical | −0.01 | −0.02 | 0 | 0 | −0.01 | +0.02 |
| Example 14, | Compound having an acetate radical | −0.03 | −0.02 | +0.02 | −0.02 | 0 | 0 |
| Example 15, | Compound having an acetate radical | −0.02 | −0.03 | +0.02 | −0.01 | −0.02 | +0.01 |
| Example 16, | Compound having an acetate radical | −0.02 | −0.02 | +0.02 | −0.02 | 0 | 0 |
| Example 17, | Compound having an acetate radical | −0.01 | −0.02 | 0 | −0.02 | −0.01 | 0 |
| Example 18, | Compound having an acetate radical | −0.02 | −0.03 | +0.01 | −0.01 | 0 | −0.01 |
| Example 19, | Compound having an acetate radical | −0.02 | −0.01 | 0 | −0.01 | 0 | 0 |
| Example 20, | Compound having an acetate radical | −0.02 | −0.03 | +0.01 | −0.02 | −0.01 | 0 |
| Example 21, | Compound having an acetate radical | −0.03 | −0.01 | 0 | −0.01 | −0.01 | −0.01 |
| Example 22, | Compound having an acetate radical | −0.03 | −0.02 | +0.02 | 0 | −0.01 | 0 |
| Example 23, | Compound having an acetate radical | −0.03 | −0.02 | 0 | −0.01 | 0 | 0 |
| Example 24, | Compound having an acetate | −0.02 | −0.03 | +0.01 | −0.02 | 0 | +0.01 |

TABLE 5-continued

Metal corrosion inhibiting performance of derivatives having a carboxylate radical of azaalkenelactams with long chain hydrocarbon radical in brake fluid composition A

| Sample added Blanc (Brake fluid composition A) | | Test metal | | | | | |
|---|---|---|---|---|---|---|---|
| | | Tin plate Weight change $-0.15$ mg/cm$^2$ | Steel Weight change $-0.20$ mg/cm$^2$ | Aluminum Weight change $+0.07$ mg/cm$^2$ | Cast iron Weight change $-0.14$ mg/cm$^2$ | Brass Weight change $-0.20$ mg/cm$^2$ | Copper Weight change $+0.18$ mg/cm$^2$ |
| Example 25, | Compound having an acetate radical | $-0.02$ | $-0.03$ | $+0.01$ | $-0.02$ | 0 | 0 |
| Example 26, | Compound having an acetate radical | $-0.01$ | $-0.03$ | $+0.01$ | $-0.02$ | $-0.01$ | $-0.02$ |
| Example 27, | Compound having an acetate radical | $-0.02$ | $-0.03$ | $+0.02$ | $-0.02$ | $-0.02$ | $-0.02$ |
| Example 28, | Compound having an acetate radical | $-0.02$ | $-0.03$ | $+0.01$ | $-0.01$ | 0 | $-0.01$ |
| Example 29, | Compound having an acetate radical | $-0.01$ | $-0.02$ | 0 | $-0.02$ | $+0.01$ | $-0.01$ |
| Example 30, | Compound having an acetate radical | $-0.03$ | $-0.03$ | $+0.01$ | $-0.02$ | $-0.02$ | $-0.01$ |
| Example 31, | Compound having an acetate radical | $-0.03$ | $-0.03$ | $+0.02$ | $-0.04$ | $-0.01$ | 0 |
| Example 32, | Compound having an acetate radical | $-0.03$ | $-0.02$ | $+0.02$ | $-0.02$ | $-0.01$ | $+0.01$ |
| Example 33, | Compound having a propionate radical | $-0.02$ | $-0.02$ | 0 | $-0.01$ | $-0.02$ | $-0.01$ |
| Example 34, | Compound having an acetate radical | $-0.02$ | $-0.03$ | $+0.02$ | $-0.03$ | $-0.01$ | 0 |
| Example 35, | Compound having an acetate radical | $-0.01$ | $-0.02$ | 0 | $-0.01$ | 0 | 0 |
| Example 36, | Compound having an acetate radical | $-0.02$ | $-0.03$ | $+0.02$ | $-0.02$ | $-0.02$ | $-0.01$ |
| Example 37, | Compound having a propionate radical | $-0.02$ | $-0.02$ | $+0.02$ | $-0.02$ | $-0.01$ | 0 |
| Example 38, | Compound having an acetate radical | $-0.01$ | $-0.02$ | $+0.02$ | $-0.01$ | 0 | $-0.01$ |
| Example 39, | Compound having an acetate radical | $-0.01$ | $-0.03$ | $+0.02$ | $-0.01$ | $-0.01$ | 0 |
| Example 40, | Compound having an acetate radical | $-0.02$ | $-0.01$ | $+0.02$ | 0 | $-0.02$ | $-0.01$ |
| Example 41, | Compound having an acetate radical | $-0.02$ | $-0.02$ | $+0.01$ | 0 | $-0.01$ | 0 |
| Example 42, | Compound having an acetate radical | $-0.02$ | $-0.03$ | $+0.01$ | $-0.02$ | 0 | 0 |
| Example 43, | Compound having an acetate radical | $-0.03$ | $-0.02$ | $+0.02$ | $-0.03$ | $-0.01$ | $-0.02$ |
| Example 44, | Compound having an acetate radical | $-0.03$ | $-0.01$ | 0 | $-0.03$ | $-0.01$ | $-0.01$ |
| Example 45, | Compound having an acetate radical | $-0.01$ | $-0.03$ | $+0.01$ | $-0.02$ | $-0.01$ | $-0.01$ |
| Example 46, | Compound having an acetate radical | $-0.03$ | $-0.03$ | $+0.02$ | $-0.02$ | 0 | $-0.01$ |
| Example 47, | Compound having an acetate radical | $-0.03$ | $-0.03$ | $+0.02$ | $-0.04$ | $-0.02$ | $-0.02$ |
| Example 48, | Compound having | $-0.01$ | $-0.02$ | 0 | $-0.02$ | $-0.01$ | $-0.01$ |

TABLE 5-continued

Metal corrosion inhibiting performance of derivatives having a carboxylate radical of azaalkenelactams with long chain hydrocarbon radical in brake fluid composition A

| Sample added Blanc (Brake fluid composition A) | | Test metal | | | | | |
|---|---|---|---|---|---|---|---|
| | | Tin plate Weight change $-0.15$ mg/cm$^2$ | Steel Weight change $-0.20$ mg/cm$^2$ | Aluminum Weight change $+0.07$ mg/cm$^2$ | Cast iron Weight change $-0.14$ mg/cm$^2$ | Brass Weight change $-0.20$ mg/cm$^2$ | Copper Weight change $+0.18$ mg/cm$^2$ |
| | a propionate radical | | | | | | |
| Example 49, | Compound having an acetate radical | −0.02 | −0.02 | +0.01 | 0 | −0.01 | −0.01 |
| Example 50, | Compound having an acetate radical | −0.02 | −0.03 | +0.02 | −0.03 | −0.01 | 0 |
| Example 51, | Compound having an acetate radical | −0.03 | −0.03 | +0.02 | −0.03 | −0.01 | 0 |
| Example 52, | Compound having an acetate radical | −0.02 | −0.03 | +0.02 | 0 | −0.01 | −0.01 |
| Example 53, | Compound having an acetate radical | −0.02 | −0.02 | +0.01 | −0.01 | 0 | −0.01 |
| Example 54, | Compound having an acetate radical | −0.02 | −0.02 | +0.02 | −0.02 | −0.02 | −0.02 |
| Example 55, | Compound having an acetate radical | −0.03 | −0.02 | +0.02 | −0.02 | −0.01 | 0 |
| Example 56, | Compound having a propionate radical | −0.02 | −0.03 | +0.02 | −0.03 | −0.01 | −0.02 |
| Example 57, | Compound having an acetate radical | −0.01 | −0.02 | +0.01 | −0.02 | 0 | −0.01 |
| Example 58, | Compound having a propionate radical | −0.03 | −0.01 | +0.01 | 0 | −0.02 | −0.02 |
| Example 59, | Compound having an acetate radical | −0.02 | −0.02 | 0 | −0.01 | −0.02 | −0.02 |
| Example 60, | Compound having a propionate radical | −0.02 | −0.02 | +0.02 | −0.02 | −0.01 | 0 |
| Example 61, | Compound having an acetate radical | −0.01 | −0.03 | +0.01 | −0.02 | 0 | −0.01 |
| Example 62, | Compound having an acetate radical | −0.02 | −0.01 | +0.01 | −0.02 | −0.01 | 0 |
| Example 63, | Compound having an acetate radical | −0.02 | −0.02 | +0.01 | −0.03 | −0.01 | 0 |
| Example 64, | Compound having an acetate radical | −0.02 | −0.01 | +0.02 | −0.03 | −0.02 | −0.02 |
| Example 65, | Compound having a propionate radical | −0.02 | −0.02 | 0 | −0.02 | −0.02 | −0.02 |
| Example 66, | Compound having an acetate radical | −0.01 | −0.02 | +0.02 | −0.01 | 0 | −0.01 |
| Example 67, | Compound having an acetate radical | −0.02 | −0.02 | +0.02 | −0.01 | −0.01 | 0 |
| Example 68, | Compound having an acetate radical | −0.03 | −0.03 | +0.01 | −0.01 | 0 | −0.01 |
| Example 69, | Compound having an acetate radical | −0.02 | −0.02 | +0.02 | −0.02 | −0.01 | 0 |
| Example 70, | Compound having an acetate radical | −0.02 | −0.02 | +0.01 | −0.03 | −0.02 | −0.02 |
| Lauryldimethylbetaine | | −0.10 | −0.19 | +0.09 | −0.15 | −0.23 | −0.15 |
| 1-Hydroxyethyl-2-unde- | | −0.12 | −0.16 | +0.10 | −0.12 | −0.24 | −0.12 |

TABLE 5-continued

Metal corrosion inhibiting performance of derivatives having a carboxylate radical of azaalkenelactams with long chain hydrocarbon radical in brake fluid composition A

| | Test metal | | | | | |
|---|---|---|---|---|---|---|
| Sample added | Tin plate Weight change | Steel Weight change | Aluminum Weight change | Cast iron Weight change | Brass Weight change | Copper Weight change |
| Blanc (Brake fluid composition A) | −0.15 mg/cm$^2$ | −0.20 mg/cm$^2$ | +0.07 mg/cm$^2$ | −0.14 mg/cm$^2$ | −0.20 mg/cm$^2$ | +0.18 mg/cm$^2$ | cylimidazolium betaine

INDUSTRIAL APPLICABILITY

Since the bactericidal surface active agents of this invention exhibit excellent bactericidal action against any of the aerobic, anaerobic, gram-positive and gram-negative bacteria, they are of high industrial applicability.

We claim:

1. A cyclic amide compound of the formula

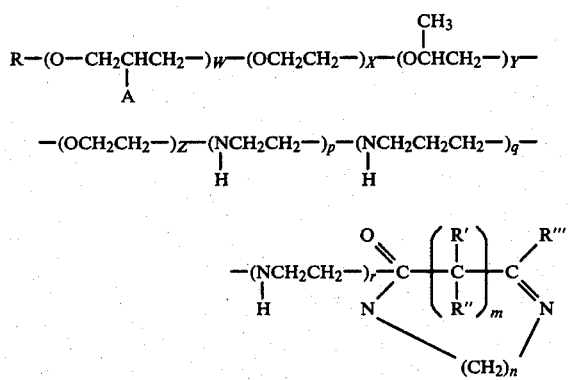

wherein R is an alkyl group, alkenyl group, monoalkylphenyl group, monoalkylbenzyl group, hydroxyalkyl group, alkylcarbonyl group, alkenylcarbonyl or hydroxysubstituted alkyl- or alkenyl-carbonyl group having 8 to 22 carbon atoms in total, R', R" and R''' are hydrogen atoms or methyl groups, A is hydrogen atom or methyl group, $0 \leq W \leq 1$, $0 \leq X+Z \leq 3$, $0 \leq Y \leq 3$, $0 \leq p+q+r \leq 3$, m=1 or 2, and n=2 or 3; said compound may assume a structure in which, if necessary, the nitrogen atoms, except for the amide grouping, may combine with a carboxylate radical by covalent bond or to add to a carboxylate.

2. A compound according to claim 1, wherein the cyclic amide is 4-dodecylaminoethyl-7-methyl-3,6-dihydro-2H-1,4-diazepin-5-one.

3. A compound according to claim 1, wherein the cyclic amide is 4-dodecylaminoethylaminoethyl-7-methyl-3,6-dihydro-2H-1,4-diazepin-5-one.

4. A compound according to claim 1, wherein the cyclic amide is 4-tetradecylaminoethyl-7-methyl-3,6-dihydro-2H-1,4-diazepin-5-one.

5. A compound according to claim 1, wherein the cyclic amide is 4-lauramidoethyl-7-methyl-3,6-dihydro-2H-1,4-diazepin-5-one.

6. A compound according to claim 1, wherein the cyclic amide is 4-(2-hydroxyhexadecyl)aminoethyl-7-methyl-3,6-dihydro-2H-1,4-diazepin-5-one.

7. A compound according to claim 1, wherein the cyclic amide is 4-tetradecylaminoethyl-6-methyl-3,6-dihydro-2H-1,4-diazepin-5-one.

8. A compound according to claim 1, wherein the cyclic amide is 4-(2-hydroxyhexadecyl)aminoethyl-6-methyl-3,6-dihydro-2H-1,4-diazepin-5-one.

9. A compound according to claim 1, wherein the cyclic amide is 1-tetradecylaminoethyl-3-methyl-3,6,7,8-tetrahydro-1,5-diazocin-2-one.

10. A compound according to claim 1, wherein the cyclic amide is 1-(2-hydroxyhexadecyl)aminoethyl-3-methyl-3,6,7,8-tetrahydro-1,5-diazocin-2-one.

11. A compound according to claim 1, wherein the cyclic amide is 4-tetradecylaminoethyl-2,3,6,7-tetrahydro-1,4-diazocin-5-one.

12. A compound according to claim 1, wherein the cyclic amide is 4-(2-hydroxyhexadecyl)aminoethyl-2,3,6,7-tetrahydro-1,4-diazocin-5-one.

13. A compound according to claim 1, wherein the cyclic amide is 4-tetradecylaminoethyl-6,6-dimethyl-3-hydro-2H-1,4-diazepin-5-one.

14. A compound according to claim 1, wherein the cyclic amide is 4-(2-hydroxyhexadecyl)aminoethyl-6,6-dimethyl-3-hydro-2H-1,4-diazepin-5-one.

15. A compound according to claim 1, wherein the cyclic amide is 1-tetradecylaminoethyl-3,3-dimethyl-6,7,8-trihydro-1,5-diazocin-5-one.

16. A compound according to claim 1, wherein the cyclic amide is 1-(2-hydroxyhexadecyl)aminoethyl-3,3-dimethyl-6,7,8-trihydro-1,5-diazocin-5-one.

17. A compound according to claim 1, wherein the cyclic amide is 4-tetradecylaminoethyl-6-methyl-2,3,6,7-tetrahydro-1,4-diazocin-5-one.

18. A compound according to claim 1, wherein the cyclic amide is 4-(2-hydroxyhexadecyl)aminoethyl-6-methyl-2,3,6,7-tetrahydro-1,4-diazocin-5-one.

19. A compound according to claim 1, wherein the cyclic amide is 4-tetradecylaminoethyl-7-methyl-1-azonia-4-azacyclohept-7-en-5-one-1-acetate.

20. A compound according to claim 1, wherein the cyclic amide is 4-lauramidoethyl-7-methyl-1-azonia-4-azacyclohept-7-en-5-one-1-acetate.

21. An antibacterial surface active composition comprising water and an antibacterially effective amount of a cyclic amide compound in accordance with claim 1.

* * * * *